(12) United States Patent
Maehara et al.

(10) Patent No.: US 11,391,720 B2
(45) Date of Patent: Jul. 19, 2022

(54) CELL POTENTIAL DETECTION APPARATUS, METHOD FOR MANUFACTURING CELL POTENTIAL DETECTION APPARATUS, AND INFORMATION PROCESSING SYSTEM

(71) Applicant: SONY SEMICONDUCTOR SOLUTIONS CORPORATION, Kanagawa (JP)

(72) Inventors: Masataka Maehara, Tokyo (JP); Masato Kawashima, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 123 days.

(21) Appl. No.: 16/651,370

(22) PCT Filed: Sep. 21, 2018

(86) PCT No.: PCT/JP2018/034977
§ 371 (c)(1),
(2) Date: Mar. 27, 2020

(87) PCT Pub. No.: WO2019/069707
PCT Pub. Date: Apr. 11, 2019

(65) Prior Publication Data
US 2020/0292523 A1 Sep. 17, 2020

(30) Foreign Application Priority Data
Oct. 5, 2017 (JP) .............................. JP2017-195062

(51) Int. Cl.
*G01N 33/483* (2006.01)
*G01N 27/327* (2006.01)
(Continued)

(52) U.S. Cl.
CPC ..... *G01N 33/48728* (2013.01); *G01N 27/301* (2013.01); *G01N 27/416* (2013.01); *G01N 33/4836* (2013.01)

(58) Field of Classification Search
CPC ................................................ G01N 33/48728
See application file for complete search history.

(56) References Cited

U.S. PATENT DOCUMENTS 6,193,866 B1 2/2001 Bader et al.
RE37,977 E 2/2003 Sugihara et al.
(Continued)

FOREIGN PATENT DOCUMENTS

CN 1284166 A 2/2001
CN 1619302 A 5/2005
(Continued)

OTHER PUBLICATIONS

Wang et al., "Chemical and physical modifications to poly(dimethylsiloxane) surfaces affect adhesion of Caco-2 cells," Journal of Biomedical Materials Research Part A, published online Oct. 13, 2009, pp. 1260-1271 (Year: 2009).*
(Continued)

*Primary Examiner* — Alexander S Noguerola
(74) *Attorney, Agent, or Firm* — Chip Law Group

(57) ABSTRACT

The present disclosure relates to a cell potential detection apparatus that can prevent a culture solution from being contaminated by a component harmful to cells, a method for manufacturing the cell potential detection apparatus, and an information processing system. The cell potential detection apparatus includes a cell potential detection chip including an electrode section configured to detect a potential of a cell, a member included in a liquid storage section configured to store a culture solution for the cell, and a film covering a liquid contact surface of the member and being harmless to
(Continued)

the cell, the liquid contact surface being configured to contact the culture solution. The present technology can be applied to, for example, a semiconductor module in which a chip for detecting a potential at an action potential generation point generated due to a chemical change in a cell is packaged.

10 Claims, 22 Drawing Sheets

(51) Int. Cl.
*G01N 33/487* (2006.01)
*G01N 27/30* (2006.01)
*G01N 27/416* (2006.01)

(56) References Cited

U.S. PATENT DOCUMENTS

| | | | | |
|---|---|---|---|---|
| 2002/0063067 | A1* | 5/2002 | Bech | B01L 3/0262 205/775 |
| 2004/0251145 | A1* | 12/2004 | Robertson | G01N 33/48728 205/775 |
| 2005/0112756 | A1 | 5/2005 | Nakatani et al. | |
| 2005/0279634 | A1 | 12/2005 | Ozaki et al. | |
| 2007/0172814 | A1* | 7/2007 | Li | C12M 25/04 435/4 |
| 2013/0008786 | A1 | 1/2013 | Hashimotodani et al. | |
| 2017/0074832 | A1* | 3/2017 | Pahlavan | G01N 29/14 |

FOREIGN PATENT DOCUMENTS

| | | |
|---|---|---|
| CN | 1809628 A | 7/2006 |
| EP | 1040345 A1 | 10/2000 |
| EP | 1147409 A1 | 10/2001 |
| EP | 1533615 A2 | 5/2005 |
| EP | 2650678 A1 | 10/2013 |
| JP | 08-062209 B2 | 3/1996 |
| JP | 11-187865 A | 7/1999 |
| JP | 2002-532715 A | 10/2002 |
| JP | 2005-156234 A | 6/2005 |
| KR | 10-0433913 B1 | 6/2004 |
| WO | 99/034202 A1 | 7/1999 |
| WO | 00/036407 A1 | 6/2000 |
| WO | 2005/001018 A1 | 1/2005 |
| WO | 2012/096162 A1 | 7/2012 |

OTHER PUBLICATIONS

International Search Report and Written Opinion of PCT Application No. PCT/JP2018/034977, dated Dec. 18, 2018, 10 pages of ISRWO.

\* cited by examiner

CELL POTENTIAL DETECTION APPARATUS, METHOD FOR MANUFACTURING CELL POTENTIAL DETECTION APPARATUS, AND INFORMATION PROCESSING SYSTEM

CROSS REFERENCE TO RELATED APPLICATIONS

This application is a U.S. National Phase of International Patent Application No. PCT/JP2018/034977 filed on Sep. 21, 2018, which claims priority benefit of Japanese Patent Application No. JP 2017-195062 filed in the Japan Patent Office on Oct. 5, 2017. Each of the above-referenced applications is hereby incorporated herein by reference in its entirety.

TECHNICAL FIELD

The technology according to the present disclosure (hereinafter also referred to as the present technology) relates to a cell potential detection apparatus, a method for manufacturing the cell potential detection apparatus, and an information processing system, and particularly to a cell potential detection apparatus that detects a potential of a cell, a method for manufacturing the cell potential detection apparatus, and an information processing system.

BACKGROUND ART

It has conventionally been proposed that a cylindrical polystyrene frame is fixed to a glass plate, with its center matching a center portion of a plurality of microelectrodes, and is filled with a culture solution in an integrated cell holding instrument including an integrated composite electrode in which the plurality of microelectrodes and drawing patterns thereof are provided on the glass plate (see PTL 1).

CITATION LIST

Patent Literature

[PTL 1]
Japanese Patent Laid-Open No. Hei 8-62209

SUMMARY

Technical Problem

In the invention described in PTL 1, however, no consideration is made for measures against contamination of the culture solution by a component harmful to cells.

The present technology has been made in view of the situations described above and is to prevent a culture solution from being contaminated by a component harmful to cells.

Solution to Problem

A cell potential detection apparatus according to a first aspect of the present technology includes a cell potential detection chip including an electrode section configured to detect a potential of a cell, a member included in a liquid storage section configured to store a culture solution for the cell, and a film covering a liquid contact surface of the member and being harmless to the cell, the liquid contact surface being configured to contact the culture solution.

A method for manufacturing a cell potential detection apparatus according to a second aspect of the present technology includes a step of covering, with a film harmless to a cell, a liquid contact surface of a member included in a liquid storage section of the cell potential detection apparatus including a cell potential detection chip including an electrode section configured to detect a potential of the cell, the liquid storage section being configured to store a culture solution for the cell, the liquid contact surface being configured to contact the culture solution.

An information processing system according to a third aspect of the present technology includes a cell potential detection section configured to detect a potential of a cell, and an information processing section configured to process a detection signal of the potential of the cell. The cell potential detection section includes: a cell potential detection chip including an electrode section configured to detect the potential of the cell, the cell potential detection chip being configured to output the detection signal, a member included in a liquid storage section configured to store a culture solution for the cell, and a film covering a liquid contact surface of the member and being harmless to the cell, the liquid contact surface being configured to contact the culture solution.

In the first aspect or the third aspect of the present technology, the liquid contact surface of the member included in the liquid storage section configured to store the culture solution for the cell is covered with the film harmless to the cell. The liquid contact surface is configured to contact the culture solution.

In the second aspect of the present technology, the liquid contact surface of the member included in the liquid storage section of the cell potential detection apparatus including the cell potential detection chip including the electrode section configured to detect the potential of the cell is covered with the film harmless to the cell. The liquid storage section is configured to store the culture solution for the cell. The liquid contact surface is configured to contact the culture solution.

Advantageous Effect of Invention

According to the first to third aspects of the present technology, it is possible to prevent a culture solution from being contaminated by a component harmful to cells.

It is noted that the effects described herein are not necessarily limitative, and any of the effects described in the present disclosure may be provided.

DESCRIPTION OF EMBODIMENTS

Hereinafter, modes for carrying out the invention (hereinafter referred to as "embodiments") will be described in detail with reference to the drawings. It is noted that the description will be made in the following order.

1. Example of Configuration of Cell Potential Detection Chip
2. First Embodiment (an example in which a liquid storage unit is used)
3. Second Embodiment (an example in which an overcoat is provided on the liquid storage unit)
4. Third Embodiment (an example in which a ring and a liquid storage sealing resin are used)
5. Fourth Embodiment (an example in which an overcoat is provided on the liquid storage sealing resin)
6. Fifth Embodiment (an example in which a liquid storage sealing section has a two-layer structure)
7. Sixth Embodiment (an example of an information processing system)
8. Modifications
9. Others

1. Example of Configuration of Cell Potential Detection Chip

First, an example of a configuration of a cell potential detection chip applied to the present technology will be described with reference to FIGS. 1 to 3.

Figure 1:
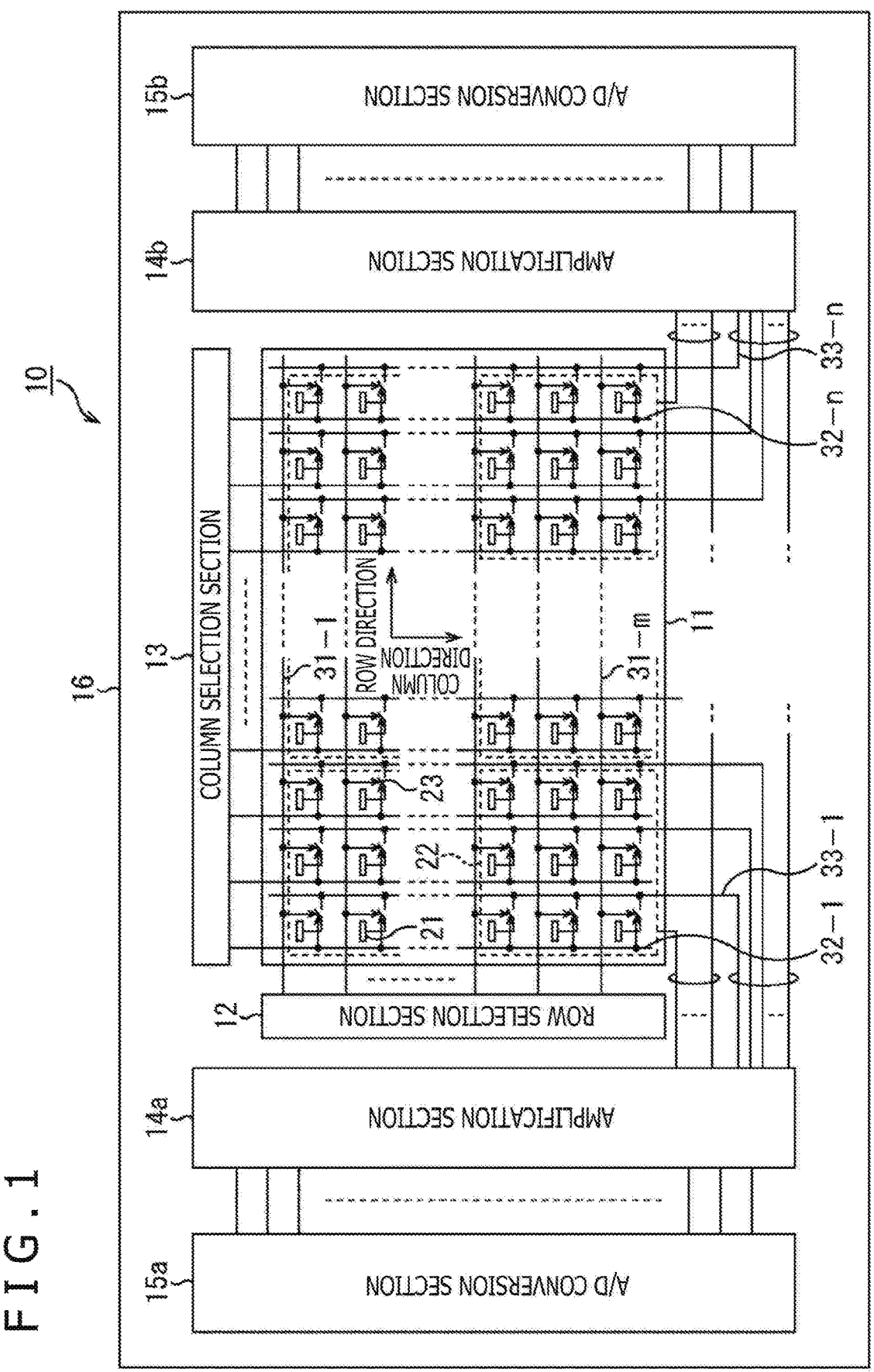
FIG. 1 is a diagram illustrating an overview of a configuration of a cell potential detection chip.

FIG. 1 is a configuration diagram illustrating an overview of a cell potential detection chip 10. The cell potential detection chip 10 is a device produced using a CMOS integrated circuit technique, with an electrode section 11, a row selection section 12, a column selection section 13, an amplification section 14A, an amplification section 14B, an A/D conversion section 15A, and an A/D conversion section 15B integrated on one semiconductor substrate 16. Here, the amplification section 14A and the A/D conversion section 15A, and the amplification section 14B and the A/D conversion section 15B, are arranged on respective sides with the electrode section 11 interposed therebetween. Alternatively, it is possible to employ another configuration in which the amplification section 14A and the A/D conversion section 15A, and the amplification section 14B and the A/D conversion section 15B, are arranged on one side of the electrode section 11.

In the electrode section 11, a plurality of readout electrodes 21, which each detects a potential at an action potential generation point generated due to a chemical change in a cell, is arranged in an array of m rows×n columns. For example, the electrode size of each readout electrode 21 is approximately equal to the size of the action potential generation point. Reference electrodes 22, which each detect a reference potential, are arranged within the array of the readout electrodes 21.

As an example here, one reference electrode 22 is arranged for each of a total of nine readout electrodes 21 of three rows×three columns. Further, the electrode size of each readout electrode 21 is smaller than the electrode size of each reference electrode 22. In other words, the electrode size of each reference electrode 22 is larger than the electrode size of each readout electrode 21. The reference potential detected by each reference electrode 22 is a base potential that serves as a base in taking the difference between the reference potential and the potential at the action potential generation point detected by the corresponding readout electrode 21. The readout electrodes 21 and the reference electrodes 22 have a planar electrode structure.

For m rows×n columns of the readout electrodes 21, row selection lines 31-1 to 31-$m$ are wired for respective rows while column selection lines 32-1 to 32-$n$ and signal readout lines 33-1 to 33-$n$ are wired for respective columns. One end of each of the row selection lines 31-1 to 31-$m$ is connected to an output terminal of a corresponding one of the rows of the row selection section 12. One end of each of the column selection lines 32-1 to 32-$n$ is connected to an output terminal of a corresponding one of the columns of the column selection section 13.

The readout electrodes 21 are connected to the signal readout lines 33-1 to 33-$n$ via switches 23. Although FIG. 1 illustrates each switch 23 as one switch for simplicity of the drawing, each switch 23 actually includes at least two switches for row selection and column selection. To correspond to this configuration, moreover, each of the signal readout lines 33-1 to 33-$n$ also includes at least two signal readout lines.

In the switches 23, for example, the switches for row selection are driven to be turned on (closed) by a row selection signal applied from the row selection section 12 via the row selection lines 31-1 to 31-$m$, while the switches for column selection are driven to be turned on by a column selection signal applied from the column selection section 13 via the column selection lines 32-1 to 32-$n$. When the switches for row selection and the switches for column selection are each turned on, the potentials detected by the readout electrodes 21 are output to the respective signal readout lines 33-1 to 33-$n$ and transmitted to the amplification section 14A and the amplification section 14B through the signal readout lines 33-1 to 33-$n$.

It is noted that while a potential readout system of the readout electrodes 21 has mainly been described here, a potential readout system of the reference electrodes 22 has a basically similar configuration. Specifically, the two potential readout systems, one for the readout electrodes 21 to read out the potentials and the other for the reference electrodes 22 to read out the potentials, are provided. Each potential readout system includes the row selection section 12, the column selection section 13, the row selection lines 31-1 to 31-$m$, the column selection lines 32-1 to 32-$n$, and the signal readout lines 33-1 to 33-$n$.

The potentials detected by the readout electrodes 21 and the potentials detected by the reference electrodes 22, which have been read out by these two potential readout systems, are supplied to the amplification section 14A and the amplification section 14B. Each of the amplification section 14A and the amplification section 14B includes a plurality of differential amplifiers provided for the plurality of readout electrodes 21 in common, and takes the difference, for each reference electrode 22 as one unit, between the potential (reference potential) detected by the reference electrode 22 and the potential detected by each of the nine readout electrodes 21 that belong to the corresponding reference electrode 22, for example. The differences are supplied to the A/D conversion section 15A and the A/D conversion section 15B. The A/D conversion section 15A and the A/D conversion section 15B perform A/D conversion on the differences output from the amplification section 14A and the amplification section 14B, and output detection signals that are digital values corresponding to the potentials detected by the readout electrodes 21.

In the cell potential detection chip 10 according to a first embodiment having the configuration described above, the reference electrodes 22 are arranged in the vicinity of the readout electrodes 21, specifically, within the array of the readout electrodes 21. In addition, the size of each reference electrode 22 is larger than the size of each readout electrode 21. Electrodes of various shapes can be used as the reference electrodes 22. FIG. 2 illustrates an example in which the reference electrodes 22 have a square electrode shape.

Figure 2:
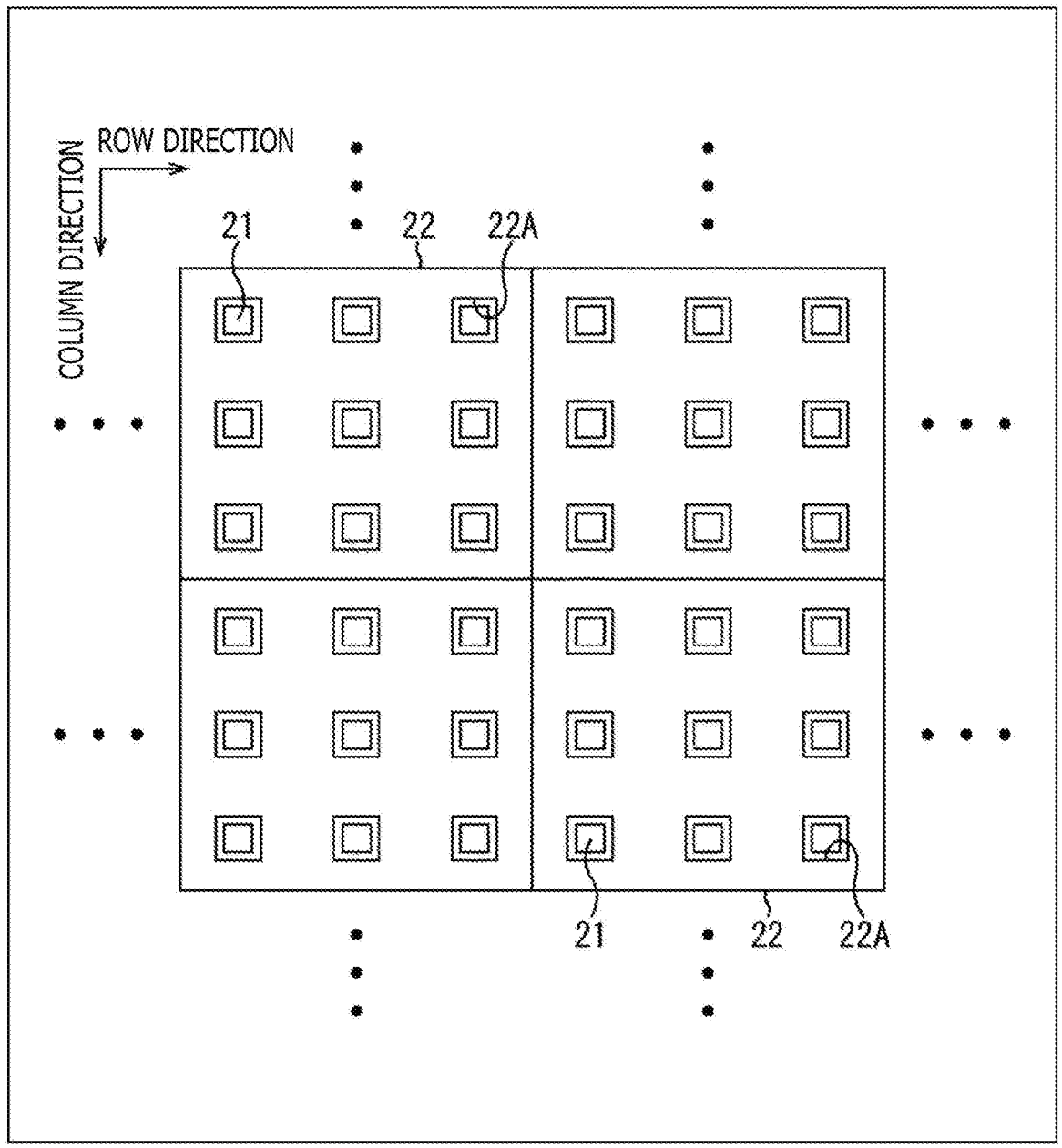
FIG. 2 is a plan view illustrating an example of electrode arrangement of reference electrodes and readout electrodes.

From a correspondence relationship with FIG. 1, FIG. 2 illustrates an example in which each reference electrode 22 is arranged for a total of nine readout electrodes 21 of three rows×three columns as one unit. Each reference electrode 22 has, in the plane thereof, nine opening sections 22A at positions corresponding to the respective nine readout electrodes 21 arranged in a matrix. In addition, each reference electrode 22 is arranged such that each of the nine readout electrodes 21 arranged in a matrix is located inside a corresponding one of the nine opening sections 22A. In other words, the readout electrodes 21 are arranged so as to be located inside the respective opening sections 22A of the corresponding reference electrode 22.

The electrode arrangement of the readout electrodes 21 and the reference electrode 22 as illustrated in FIG. 2 is suitable to read out a local potential change. As an example, in order to read out the action potential (hereinafter also simply referred to as the potential) of each living cell having a size of approximately 5 μm, the readout electrodes 21 each having an electrode size of approximately 5 μm and the reference electrode 22 having a size that is 10 times or greater the size of each readout electrode 21, that is, 50 μm or greater, are arranged.

In such a case, the action potential generation portion is equivalent to one local point. A potential variation in the reference electrode 22 having a size of 50 μm is approximately 10 times that in the readout electrode 21 having a size of 5 μm. In addition, the action potential of the living cell can be measured by taking the difference between the potential detected by each readout electrode 21 and the potential detected by the reference electrode 22.

Figure 3:
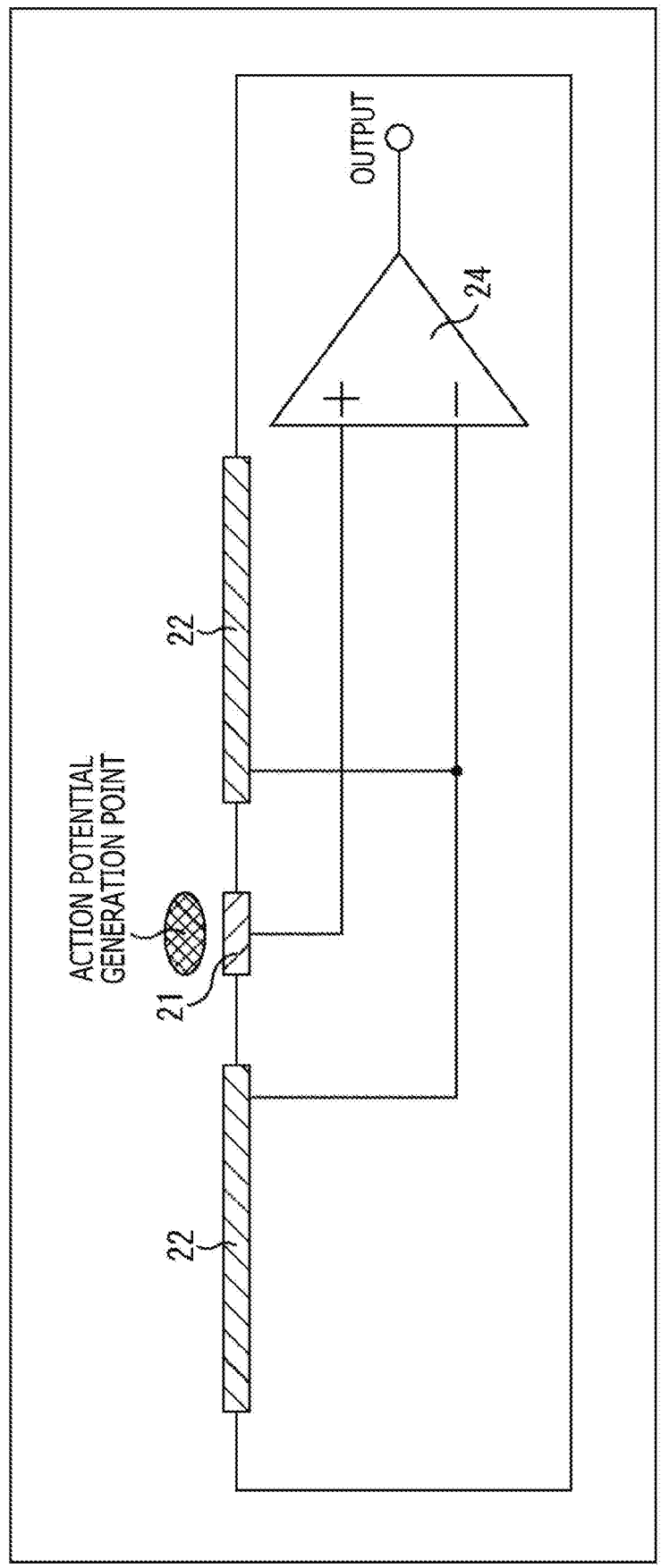
FIG. 3 is a schematic diagram illustrating an example of wiring structure between the following: a readout electrode and a reference electrode, and a differential amplifier.

FIG. 3 illustrates an example of wiring between the following: the readout electrode 21 and the reference electrode 22, and one differential amplifier of the amplification sections 14A and 14B. As described above, the reference electrode 22 is arranged in the vicinity of the readout electrodes 21, more specifically, within the array of the readout electrodes 21. With this configuration, the position of the readout electrode 21 relative to the position of a differential amplifier 24 can be equivalent to the position of the reference electrode 22 relative to the position of the differential amplifier 24. Accordingly, two wires connecting the readout electrode 21 and the reference electrode 22 to two respective input terminals of the differential amplifier 24 are substantially electrically equivalent in wiring capacity and capacity with the environment, and thus noises superimposed on these wires can be equivalent to each other. Therefore, noise included in the output of the differential amplifier 24 when the difference is taken can be suppressed.

2. First Embodiment

Next, the first embodiment of the present technology will be described with reference to FIGS. 4 to 6.

Example of Configuration of Cell Potential Detection Apparatus

Figure 4:
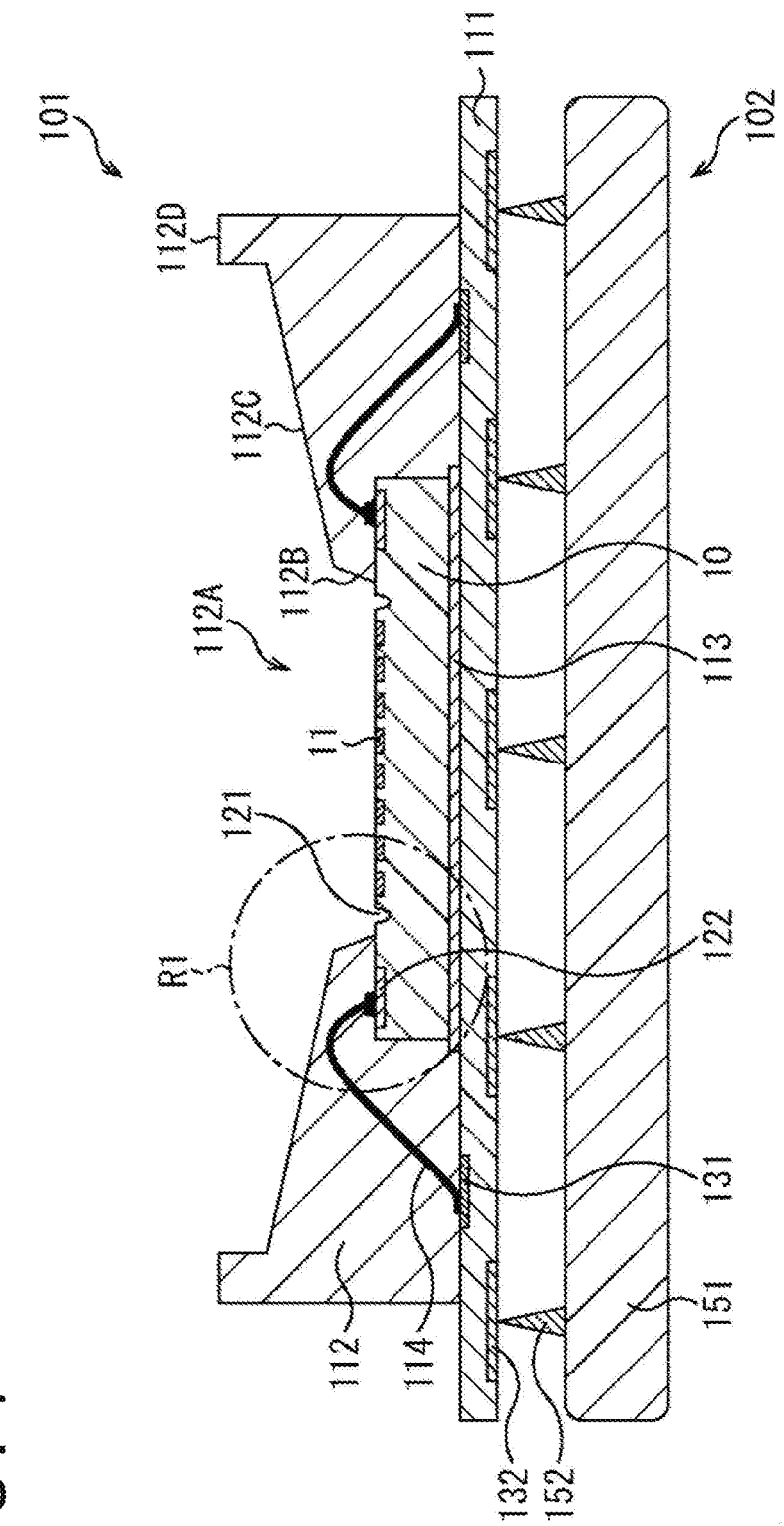
FIG. 4 is a cross-sectional view schematically illustrating a first embodiment of a cell potential detection apparatus.

FIG. 4 is a cross-sectional view schematically illustrating a cell potential detection apparatus 101 according to the first embodiment of the present technology. FIG. 5 is a plan view schematically illustrating the cell potential detection apparatus 101.

The cell potential detection apparatus 101 is a semiconductor module in which the cell potential detection chip 10 is packaged. The cell potential detection apparatus 101 includes the cell potential detection chip 10, a substrate 111, and a liquid storage unit 112.

The cell potential detection chip 10 is bonded to a substantially center of a predetermined surface (hereinafter referred to as a part surface) of the substrate 111 using a die bond paste 113.

A groove-like slit dam 121 is formed on a surface (hereinafter referred to as a detection surface) of the cell potential detection chip 10 on which the electrode section 11 is arranged. The slit dam 121 surrounds the periphery of the electrode section 11. When the liquid storage unit 112 is formed, for example, the slit dam 121 suppresses a flow of a resin included in the liquid storage unit 112 into the electrode section 11. It is noted that the illustration of the slit dam 121 is omitted in FIG. 5.

A plurality of pads 122 is arranged at the periphery of the slit dam 121, and the periphery of the electrode section 11 is surrounded by the plurality of pads 122.

A plurality of pads 131 is arranged on the part surface of the substrate 111 so as to surround the periphery of the cell potential detection chip 10. The pads 122 of the cell potential detection chip 10 correspond one-to-one with the pads 131 of the substrate 111, and each of the corresponding pads 122 and 131 is connected by a corresponding one of wires 114.

A plurality of circular external terminals 132 is arranged in a grid on a surface (hereinafter referred to as a back surface) of the substrate 111 that is opposite to the part surface. Further, each external terminal 132 is plated with Au so as not to corrode. For example, each external terminal 132 is connected to a corresponding one of pins 152 provided on a base 151 of a socket 102. In addition, the cell potential detection apparatus 101 is electrically connected to external equipment via the socket 102 and outputs, for example, a detection signal indicating a detection result of the potential of a cell to the external equipment.

The liquid storage unit 112 has a function of storing a culture solution for arranging and culturing cells and functions of sealing and protecting a connection section (hereinafter referred to as an electrical connection section) in which the cell potential detection chip 10 and the substrate 111 are electrically connected to each other.

Specifically, a rectangular opening section 112A is formed in the center of the liquid storage unit 112. The opening section 112A surrounds the periphery of the slit dam 121 on the detection surface of the cell potential detection chip 10 and exposes the electrode section 11 on the outside.

The periphery of the opening section 112A is surrounded by an inclined surface 112B. The inner periphery of the inclined surface 112B is in contact with the detection surface of the cell potential detection chip 10. The inclined surface 112B is inclined so as to increase in height from the inner periphery toward the outer periphery. The periphery of the inclined surface 112B is surrounded by an inclined surface 112C. The inclined surface 112C is inclined so as to increase in height from the inner periphery toward the outer periphery more gradually than the inclined surface 112B. A liquid contact surface with which the culture solution contacts includes the inclined surface 112B and the inclined surface 112C. The periphery of the inclined surface 112C is surrounded by a vertical wall 112D.

This configuration forms a substantially rectangular dish-shaped liquid storage section with its periphery surrounded by the inclined surface 112B, the inclined surface 112C, and the inner wall of the wall 112D. The bottom surface of the liquid storage section is an exposure section that includes the electrode section 11 and that is exposed by the opening section 112A on the detection surface of the cell potential detection chip 10. By storing the culture solution in the liquid storage section, cells arranged on the electrode section 11 can be immersed and cultured in the culture solution.

It is noted that in order not to damage the cells, the liquid storage unit 112 uses a harmless stabilizer that does not include a component harmful to the cells. For example, an epoxy resin or a silicone resin is used for the liquid storage unit 112.

The side surface of the liquid storage unit 112 stands outside the pads 131 on the part surface of the substrate 111 in a direction perpendicular to the part surface of the substrate 111. In addition, the periphery of the electrode section 11 (exposure section) on the detection surface of the cell potential detection chip 10 and the periphery of the cell potential detection chip 10 on the part surface of the substrate 111 are sealed by the liquid storage unit 112. Accordingly, the electrical connection section, which includes each pad 122 of the cell potential detection chip 10, each pad 131 of the substrate 111, and each wire 114 connecting the corresponding pads 122 and 131 to each other, is sealed by the liquid storage unit 112.

Figure 5:
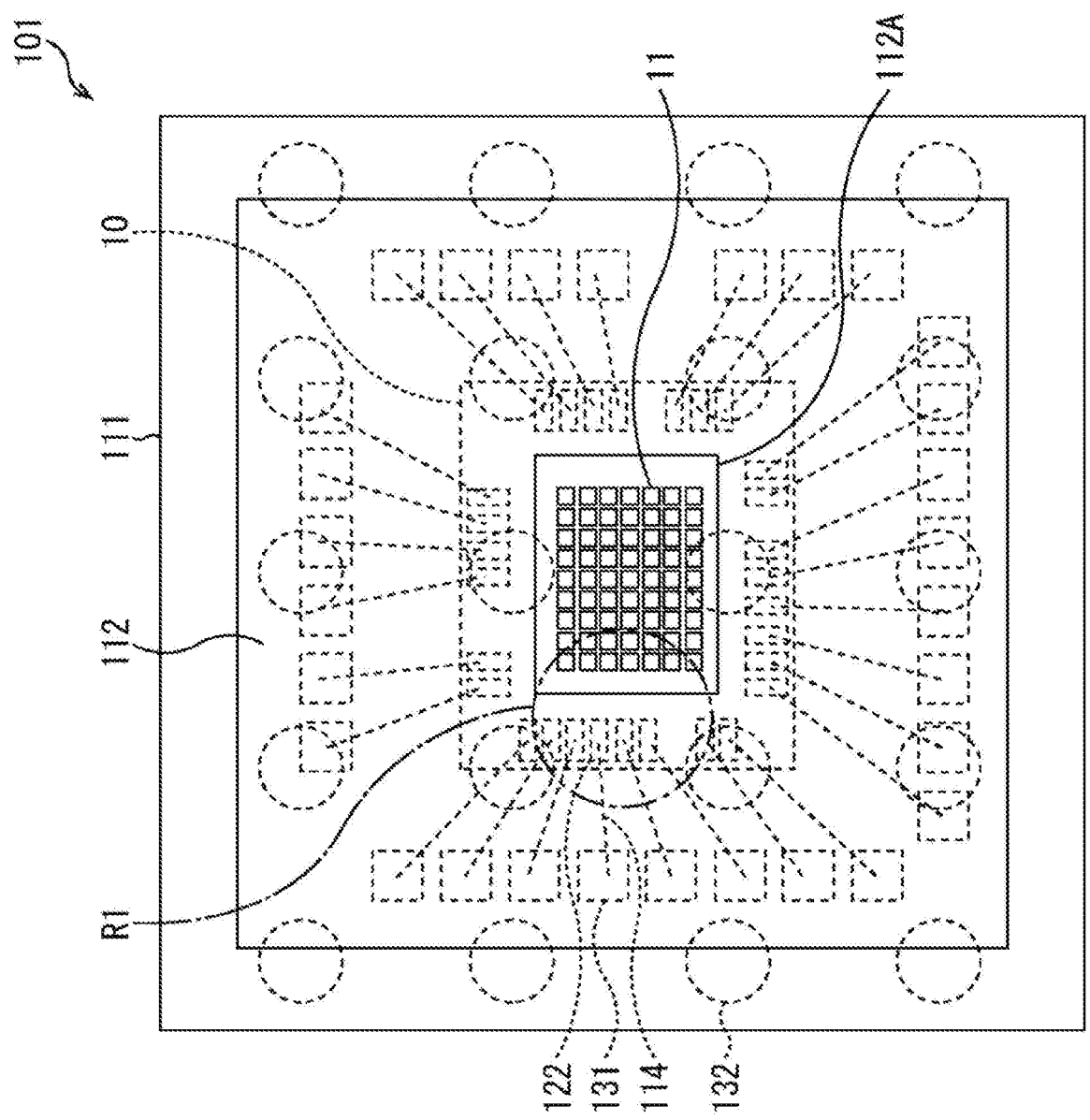
FIG. 5 is a plan view schematically illustrating the first embodiment of the cell potential detection apparatus.
Figure 6:
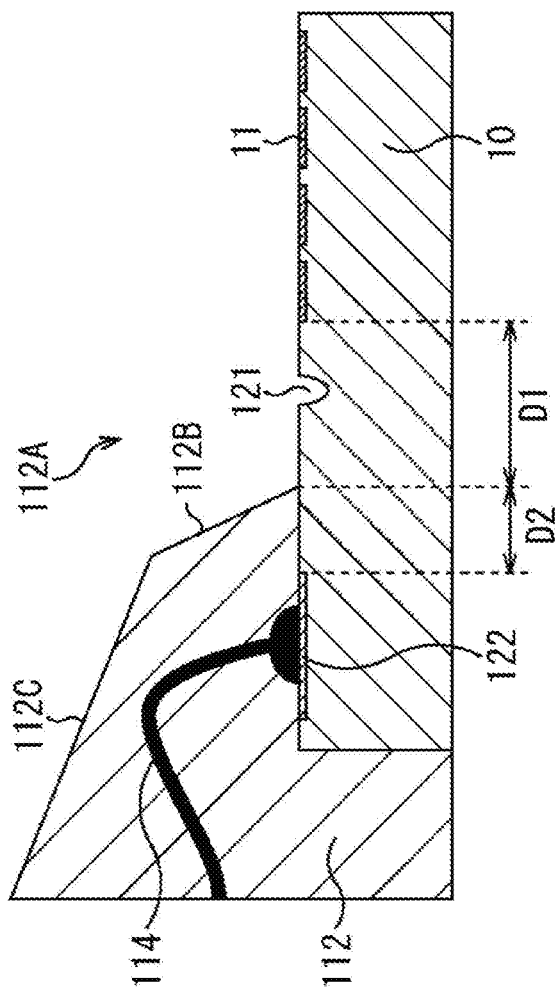
FIG. 6 is an enlarged view of an end portion of a cell potential detection chip of the cell potential detection apparatus in FIG. 4.

FIG. 6 is an enlarged view of a region R1 circled by a dashed-and-dotted line in FIGS. 4 and 5.

A distance D1 between the outer periphery of the electrode section 11 and the inner periphery of the liquid storage unit 112 (the outer periphery of the opening section 112A) is set to equal to or greater than 100 µm, for example. Further, a distance D2 between the inner periphery of the liquid storage unit 112 and the sides of the pads 122 on the electrode section 11 side is set to equal to or greater than 50 µm, for example.

With the liquid storage unit 112 provided in this manner, a necessary amount of culture solution can be stored to culture the cells regardless of the sizes of the cells. Further, the electrical connection section for the cell potential detection chip 10 and the substrate 111 can be sealed and protected by the liquid storage unit 112. Moreover, the liquid storage unit 112 has both the function of storing the culture solution and the function of sealing the electrical connection section for the cell potential detection chip 10 and the substrate 111. This configuration can, therefore, reduce the number of parts and improve the productivity.

3. Second Embodiment

Next, a second embodiment of the present technology will be described with reference to FIGS. 7 to 10.

Example of Configuration of Cell Potential Detection Apparatus

Figure 7:
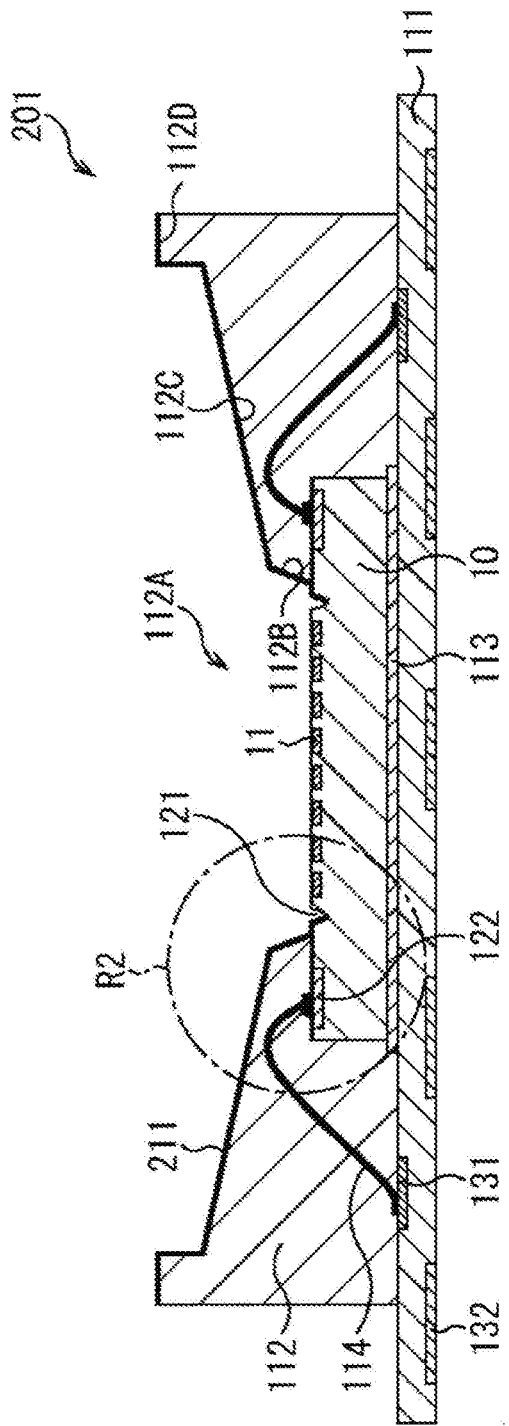
FIG. 7 is a cross-sectional view schematically illustrating a second embodiment of the cell potential detection apparatus.

FIG. 7 is a cross-sectional view schematically illustrating a cell potential detection apparatus 201 according to the second embodiment of the present technology. It is noted that in this figure, parts corresponding to the parts of the cell potential detection apparatus 101 in FIG. 4 are denoted with the same reference signs.

The cell potential detection apparatus 201 is different from the cell potential detection apparatus 101 in that an overcoat 211 is formed.

The overcoat 211 is a film that covers at least the surface of the liquid storage unit 112 with which the culture solution contacts in a case where the culture solution is stored in the liquid storage section of the cell potential detection apparatus 201. Specifically, the overcoat 211 covers an inclined surface 112B, an inclined surface 112C, and the inner wall of a wall 112D of the liquid storage unit 112. It is noted that in this example, the overcoat 211 also covers the upper surface of the wall 112D, a space between the outer periphery of the opening section 112A and the slit dam 121, and a slope from the outer periphery of the slit dam 121 to the bottom thereof.

In order not to damage the cells, the overcoat 211 includes a harmless thin film that does not include a component harmful to the cells. For example, a thin film having a thickness of approximately 10 to 1000 nm and including $SiO_2$ (silicon oxide), SiON (silicon oxynitride), $Al_2O_3$ (aluminum oxide), an epoxy resin, a silicone resin, or the like is used for the overcoat 211. It is noted that the overcoat 211 may be a multilayer film in which a plurality of thin films is stacked. Further, there is no problem even if the overcoat 211 has a film thickness of 1000 nm or greater.

Figure 8:
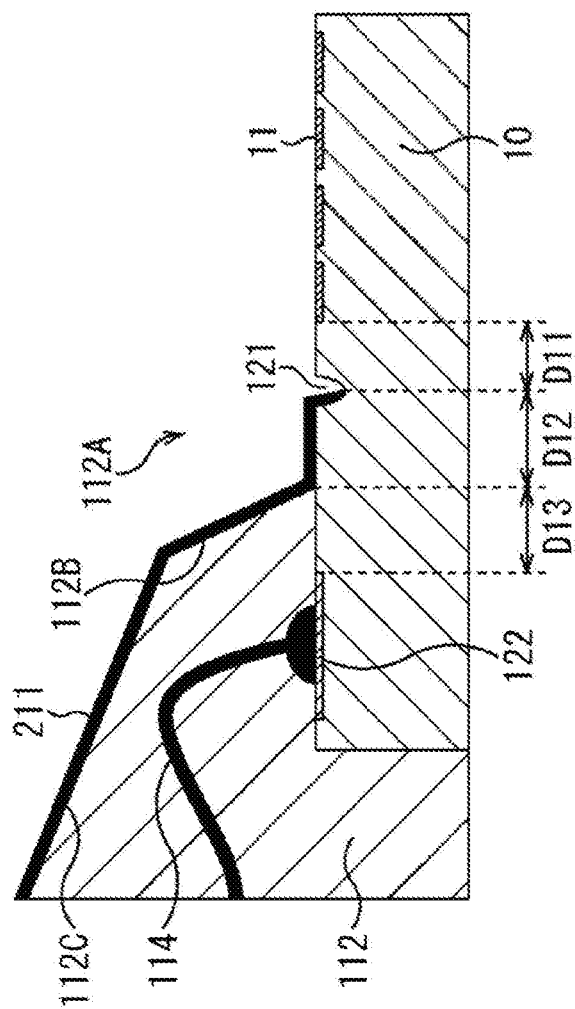
FIG. 8 is an enlarged view of an end portion of the cell potential detection chip of the cell potential detection apparatus in FIG. 7.

FIG. 8 is an enlarged view of a region R2 circled by a dashed-and-dotted line in FIG. 7.

A distance D11 between the outer periphery of the electrode section 11 and the inner periphery of the overcoat 211 is set to equal to or greater than 50 µm, for example. A distance D12 between the inner periphery of the overcoat 211 and the inner periphery of the liquid storage unit 112 (the outer periphery of the opening section 112A) is set to equal to or greater than 50 μm, for example. A distance D13 between the inner periphery of the liquid storage unit 112 and the sides of the pads 131 on the electrode section 11 side is set to equal to or greater than 50 μm, for example, similarly to the distance D2 in FIG. 6.

Method for Manufacturing Cell Potential Detection Apparatus

Next, a method for manufacturing the cell potential detection apparatus 201 will be described with reference to FIGS. 9 and 10. It is noted that in these figures, the description of the reference signs of the parts that are not necessary for the description is omitted as appropriate. Further, the illustration of the external terminals 132 of the substrate 111 is omitted.

Prior to step P1, a resist 251 is formed by a lift-off step so as to cover the electrode section 11 in each cell potential detection chip 10 of a semiconductor wafer (not illustrated) on which a plurality of cell potential detection chips 10 is formed. Then, each cell potential detection chip 10 is separated individually.

In step P1, the individually separated cell potential detection chip 10 is bonded (die-bonded) to the part surface of the substrate 111 using the die bond paste 113.

In step P2, wire bonding is performed. That is, each pad 122 of the cell potential detection chip 10 and each pad 131 of the substrate 111 are connected to each other by a corresponding one of the wires 114. At this time, for example, a collet is used so that foreign matter does not contact the resist 251.

In step P3, the liquid storage unit 112 is formed by injection molding. For example, the resin that is included in the liquid storage unit 112 is poured into a mold and then cured by a method similar to a mold step. Accordingly, the liquid storage unit 112 is formed and the periphery of the electrode section 11 on the detection surface of the cell potential detection chip 10 and the periphery of the cell potential detection chip 10 on the part surface of the substrate 111 are sealed. At this time, the slit dam 121 prevents the resin from flowing into the electrode section 11.

In step P4, the overcoat 211 is formed on the surface of the cell potential detection apparatus 201. For example, vapor deposition, electrostatic coating, inkjet, or the like is used as a method of forming the overcoat 211. At this time, the resist 251 prevents the overcoat 211 from adhering to the electrode section 11. It is noted that the overcoat 211 may adhere to the side surface of the liquid storage unit 112 and the part surface of the substrate 111.

In step P5, the resist 251 is removed by a wet process. As a result, the electrode section 11 is exposed to the outside.

It is noted that each cell potential detection apparatus 201 may be separated individually, after the plurality of cell potential detection chips 10 is bonded to a collective substrate in step P1 and the resist 251 of each cell potential detection chip 10 is removed at a time in step P5.

The cell potential detection apparatus 201 is manufactured as described above.

Since the cell potential detection apparatus 201 is provided with the overcoat 211 as described above, a member including a component harmful to the cells can be used for the liquid storage unit 112.

Further, with an inorganic material used for the overcoat 211, for example, a flame sterilization or disinfection process can be performed on the cell potential detection apparatus 201.

4. Third Embodiment

Next, a third embodiment of the present technology will be described with reference to FIGS. 11 and 12.

Example of Configuration of Cell Potential Detection Apparatus

Figure 11:
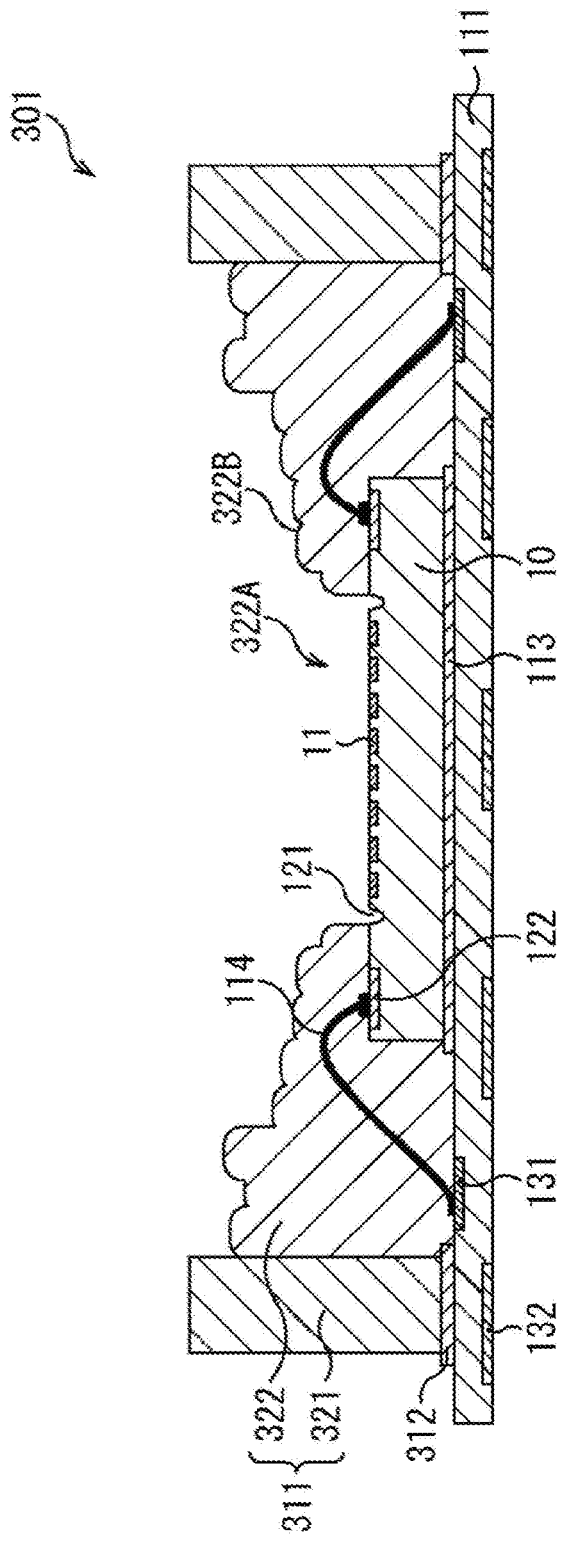
FIG. 11 is a cross-sectional view schematically illustrating a third embodiment of the cell potential detection apparatus.
Figure 12:
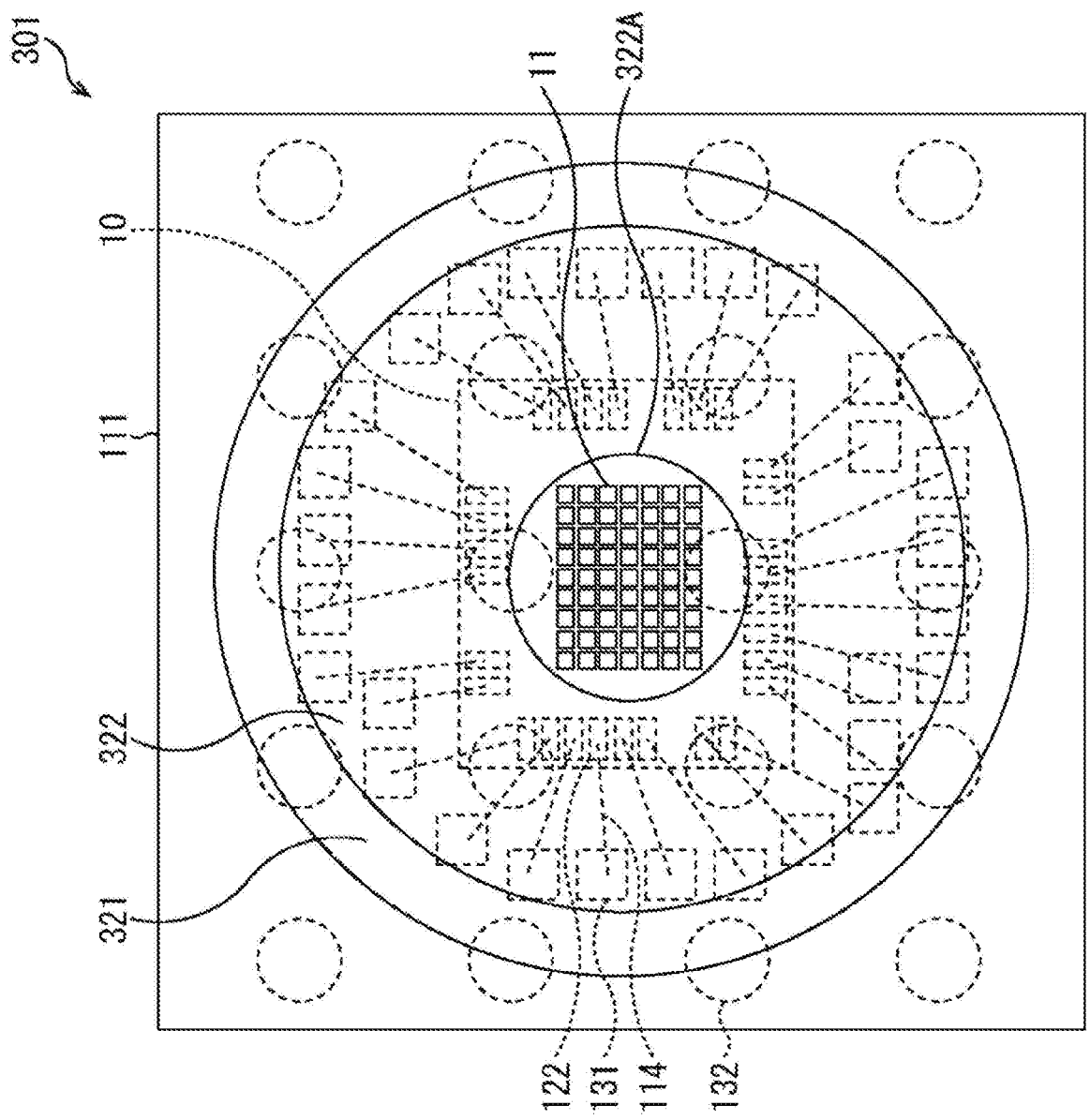
FIG. 12 is a plan view schematically illustrating the third embodiment of the cell potential detection apparatus.

FIG. 11 is a cross-sectional view schematically illustrating a cell potential detection apparatus 301 according to the third embodiment of the present technology. FIG. 12 is a plan view schematically illustrating the cell potential detection apparatus 301. It is noted that in these figures, parts corresponding to the parts of the cell potential detection apparatus 101 in FIGS. 4 and 5 are denoted with the same reference signs.

The cell potential detection apparatus 301 is different from the cell potential detection apparatus 101 in that a liquid storage sealing section 311 is provided instead of the liquid storage unit 112.

The liquid storage sealing section 311 has a function of storing the culture solution and functions of sealing and protecting the electrical connection section for the cell potential detection chip 10 and the substrate 111, as is the case of the liquid storage unit 112 of the cell potential detection apparatus 101. The liquid storage sealing section 311 includes a ring 321 and a liquid storage sealing resin 322.

The ring 321 is a cylindrical glass ring and is bonded to the part surface of the substrate 111 by a seal resin 312. The outer wall of the ring 321 surrounds the outside of the region in which the pads 131 of the substrate 111 are arranged. That is, all the pads 131 are arranged in the region surrounded by the outer wall of the ring 321. It is noted that a part of the ring 321 may overlap with a part of the pads 131. However, the inner wall of the ring 321 is arranged outside a portion of each pad 131 that is bonded to the corresponding wire 114. That is, the portions of all the pads 131 that are bonded to the respective wires 114 are arranged inside the region surrounded by the inner wall of the ring 321. It is noted that a member other than glass can also be used for the ring 321.

The liquid storage sealing resin 322 is filled between the outer periphery of the slit dam 121 on the detection surface of the cell potential detection chip 10 and the inner wall of the ring 321. The electrical connection section for the cell potential detection chip 10 and the substrate 111 is sealed and protected by the liquid storage sealing resin 322.

Further, a circular opening section 322A is formed in the center of the liquid storage sealing resin 322. The opening section 322A surrounds the outer periphery of the slit dam 121 and exposes the electrode section 11 to the outside.

The periphery of the opening section 322A is surrounded by an inclined surface 322B. The inner periphery of the inclined surface 322B is in contact with the detection surface of the cell potential detection chip 10. Further, while the inclined surface 112B has an uneven surface, the inclined surface 112B is inclined so as to gradually increase in height from the inner periphery to the outer periphery. The outer periphery of the inclined surface 322B is lower than the ring 321. In other words, the outer periphery of the inclined surface 322B is surrounded by a wall including the ring 321. A liquid contact surface with which the culture solution contacts includes the inclined surface 322B.

In addition, this configuration forms a substantially circular dish-shaped liquid storage section with its periphery surrounded by the inclined surface 322B and the inner wall of the ring 321. The bottom surface of the liquid storage section is an exposure section that includes the electrode section 11 and that is exposed by the opening section 322A on the detection surface of the cell potential detection chip 10. By storing the culture solution in the liquid storage section, the cells arranged on the electrode section 11 can be immersed and cultured in the culture solution.

It is noted that a member similar to the liquid storage unit 112 of the cell potential detection apparatus 101 in FIG. 4 is used for the liquid storage sealing resin 322.

5. Fourth Embodiment

Figure 14:
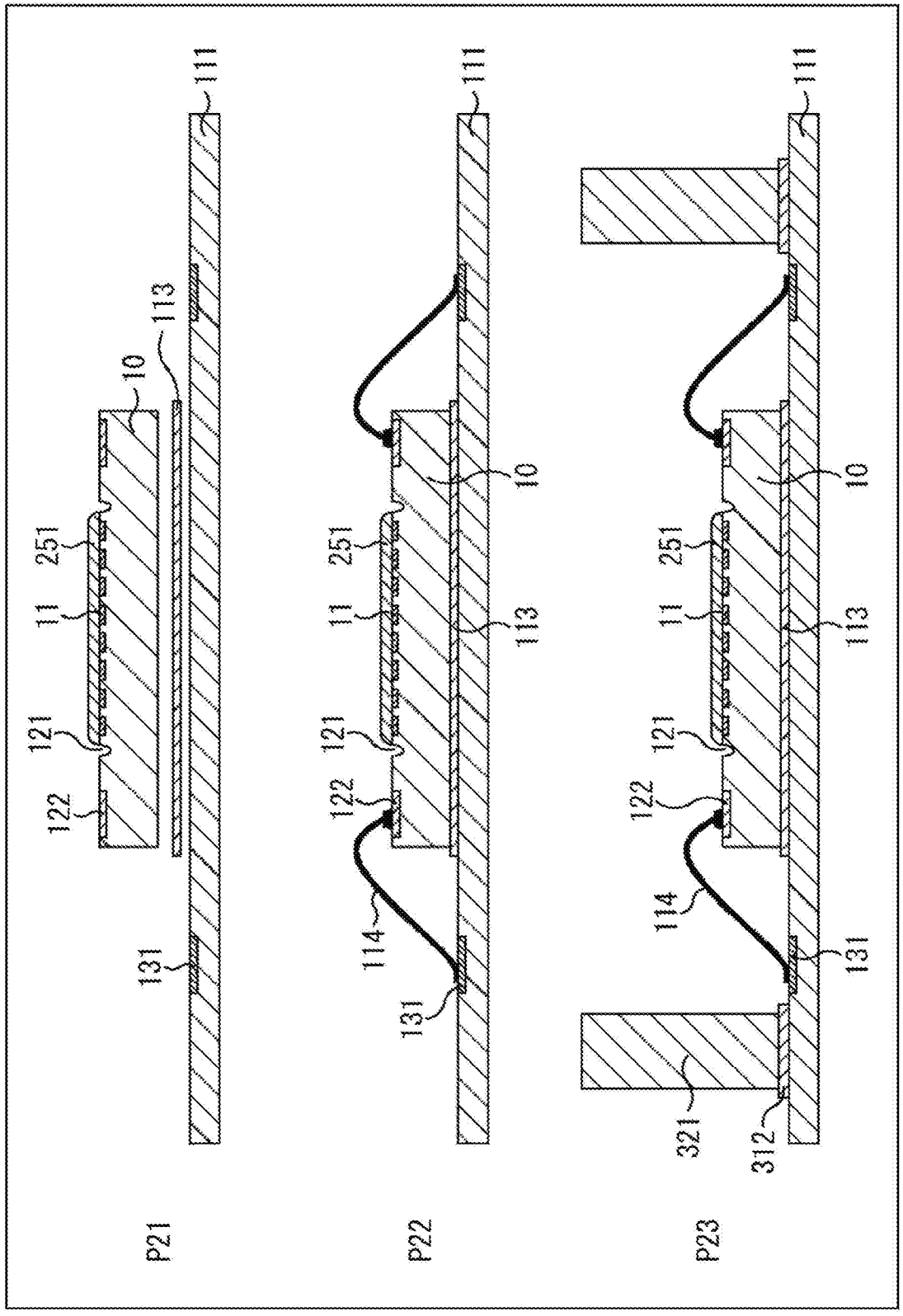
FIG. 14 is a diagram for describing a method for manufacturing the cell potential detection apparatus in FIG. 13.
Figure 15:
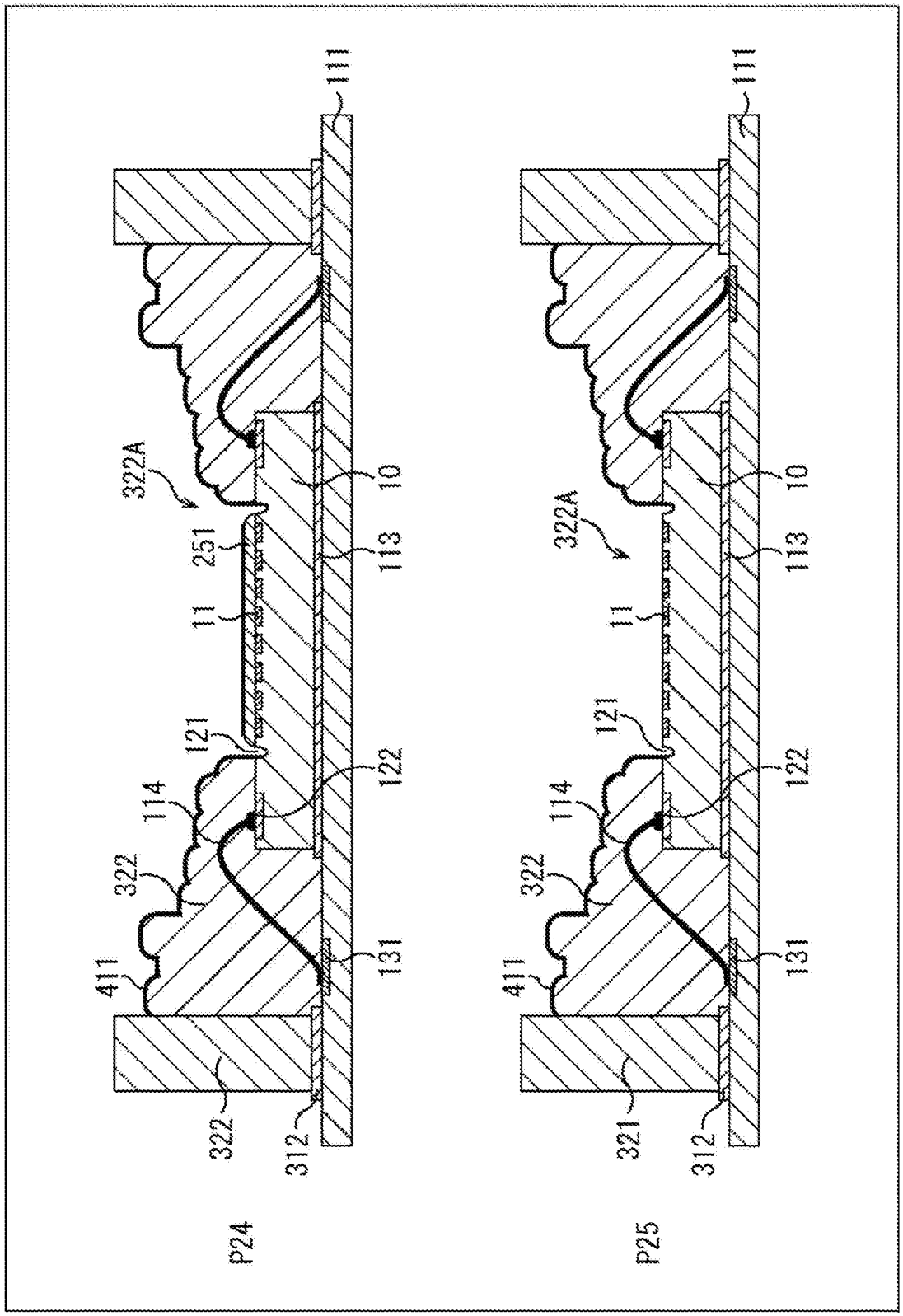
FIG. 15 is a diagram for describing the method for manufacturing the cell potential detection apparatus in FIG. 13.

Next, a fourth embodiment of the present technology will be described with reference to FIGS. 13 to 15.

Example of Configuration of Cell Potential Detection Apparatus

Figure 13:
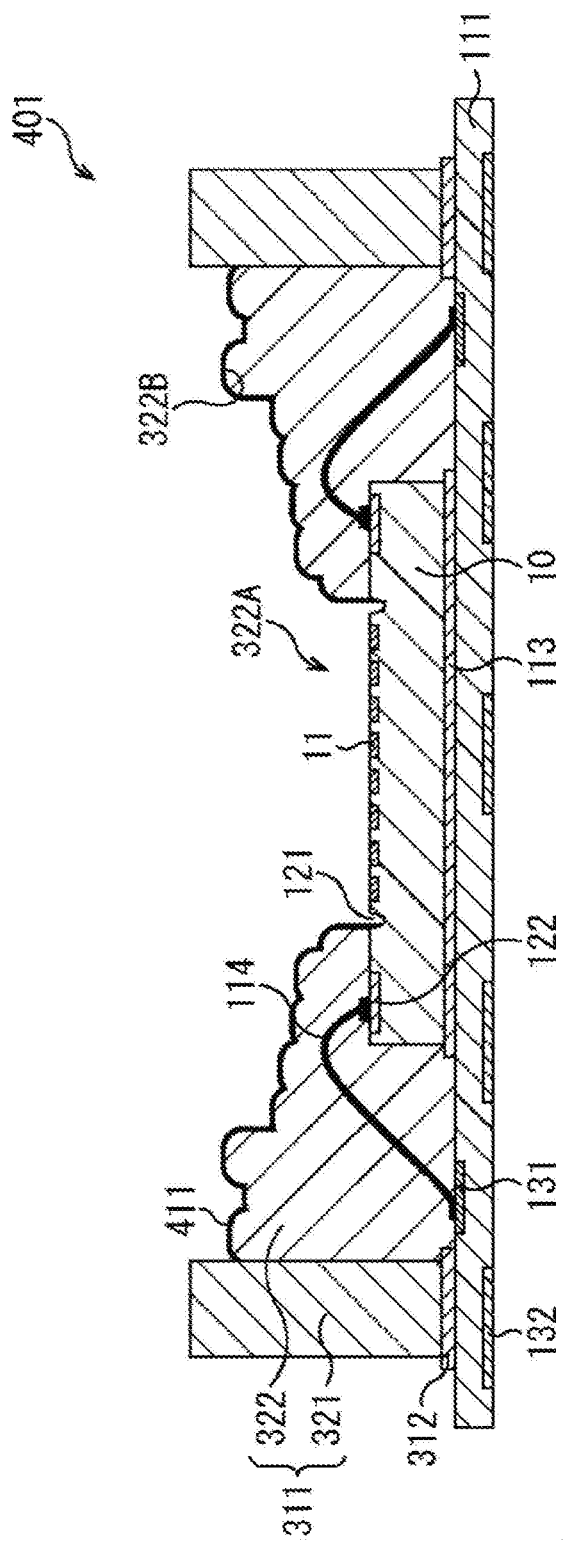
FIG. 13 is a cross-sectional view schematically illustrating a fourth embodiment of the cell potential detection apparatus.

FIG. 13 is a cross-sectional view schematically illustrating a cell potential detection apparatus 401 according to the fourth embodiment of the present technology. It is noted that in this figure, parts corresponding to the parts of the cell potential detection apparatus 301 in FIG. 11 are denoted with the same reference signs.

The cell potential detection apparatus 401 is different from the cell potential detection apparatus 301 in that an overcoat 411 is formed.

The overcoat 411 is a film that covers at least the surface of the liquid storage sealing resin 322 with which the culture solution contacts in a case where the culture solution is stored in a liquid storage section of the cell potential detection apparatus 401. Specifically, the overcoat 411 covers the inclined surface 322B of the liquid storage sealing resin 322. It is noted that in this example, the overcoat 411 also covers the slope from the outer periphery of the slit dam 121 to the bottom thereof.

A film similar to the overcoat 211 of the cell potential detection apparatus 301 in FIG. 7 is used for the overcoat 411.

With the overcoat 411 provided as described above, a member including a component harmful to the cells can be used for the liquid storage sealing resin 322.

Method for Manufacturing Cell Potential Detection Apparatus

Next, a method for manufacturing the cell potential detection apparatus 401 will be described with reference to FIGS. 14 and 15. It is noted that in these figures, the description of the reference signs of the parts that are not necessary for the description is omitted as appropriate. Further, the illustration of the external terminals 132 of the substrate 111 is omitted.

Figure 9:
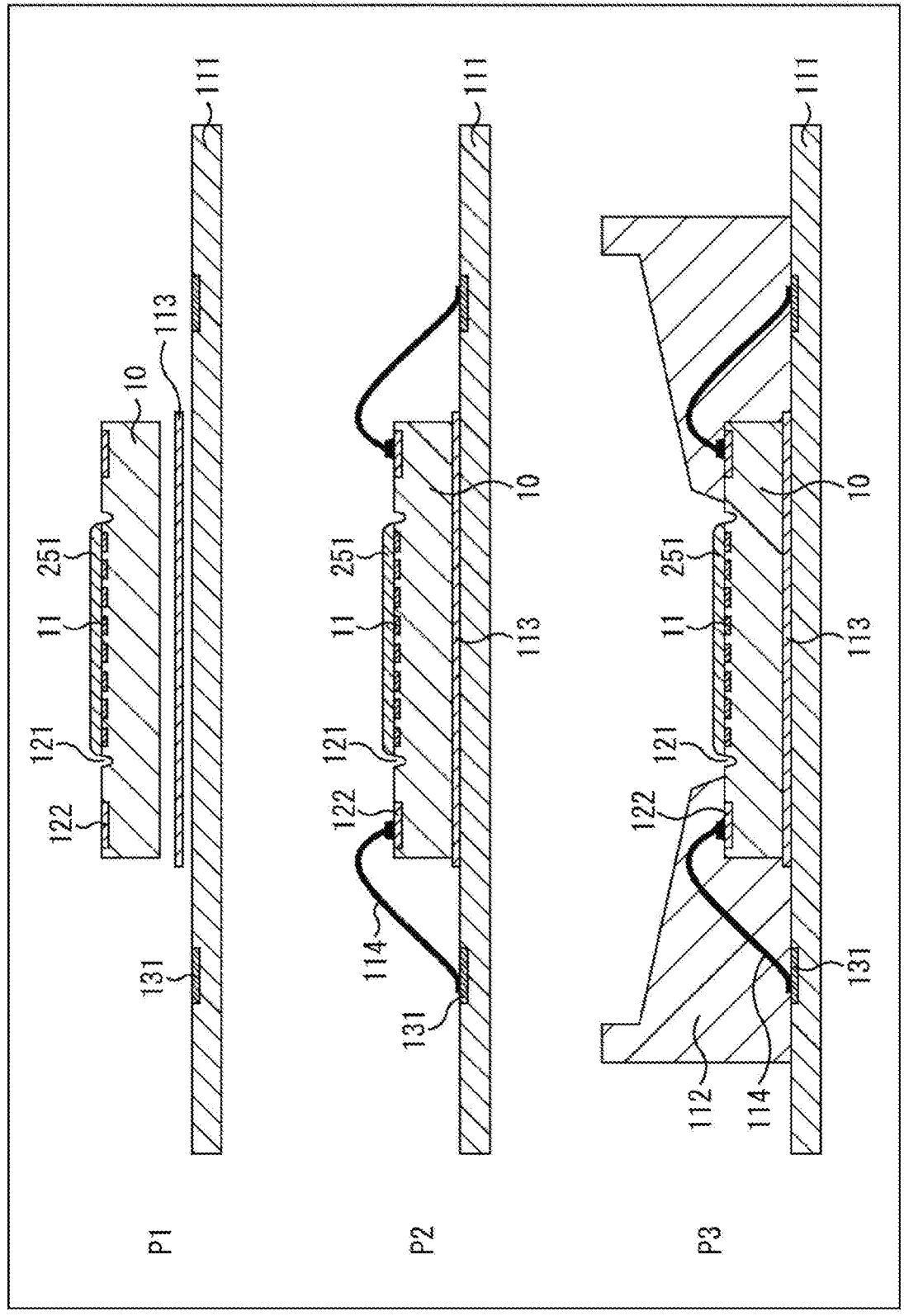
FIG. 9 is a diagram for describing a method for manufacturing the cell potential detection apparatus in FIG. 7.

Step P21 and step P22 are similar to step P1 and step P2 in FIG. 9. That is, the cell potential detection chip 10 is bonded to the part surface of the substrate 111, and each pad 122 of the cell potential detection chip 10 and each pad 131 of the substrate 111 are connected to each other by a corresponding one of the wires 114.

In step P23, the ring 321 is fixed to the substrate 111. Specifically, the seal resin 312 is applied to a part of the part surface of the substrate 111 to which the ring 321 is bonded. Then, the ring 321 is bonded onto the seal resin 312. Next, a curing process is performed. With the seal resin 312 cured, the ring 321 is fixed on the substrate 111.

In step P24, a resin is dispensed (applied) or potted (injected) at the periphery of the electrode section 11 of the cell potential detection chip 10 inside the ring 321, thereby forming the liquid storage sealing resin 322. At this time, the slit dam 121 prevents the resin from flowing into the electrode section 11. Next, the overcoat 411 is formed on the surface of the cell potential detection apparatus 401 by a process similar to step P4 in FIG. 10. It is noted that the overcoat 411 may adhere to the ring 321 and the part surface of the substrate 111.

Figure 10:
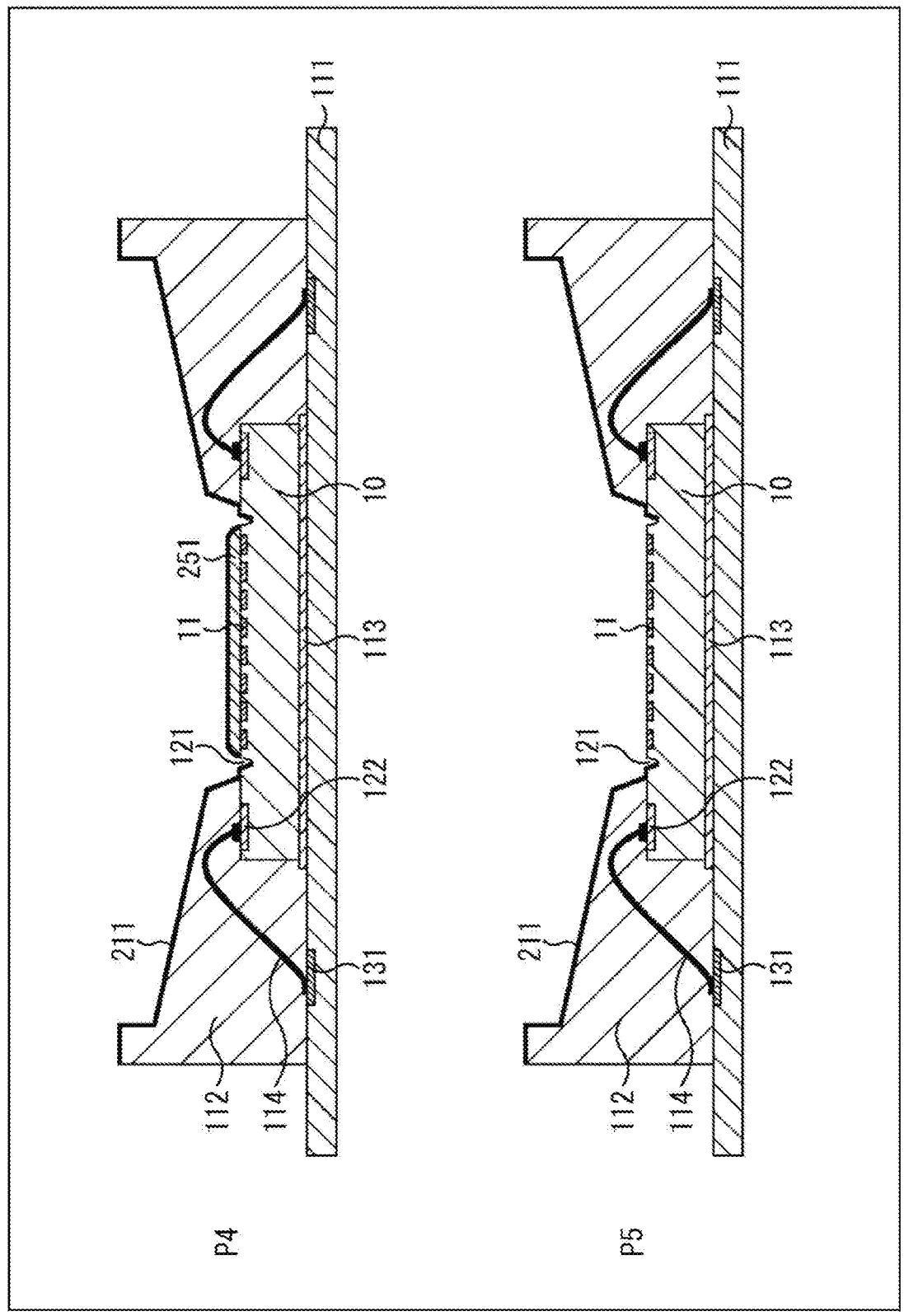
FIG. 10 is a diagram for describing the method for manufacturing the cell potential detection apparatus in FIG. 7.

In step P25, the resist 251 is removed by a process similar to step P5 in FIG. 10.

The cell potential detection apparatus 401 is manufactured as described above.

Since the cell potential detection apparatus 401 is provided with the overcoat 411 as described above, a member including a component harmful to the cells can be used for the liquid storage sealing resin 322.

Further, with an inorganic material used for the overcoat 411, for example, the flame sterilization or disinfection process can be performed on the cell potential detection apparatus 401.

6. Fifth Embodiment

Next, a fifth embodiment of the present technology will be described with reference to FIGS. 16 to 21.

Usually, the sterilization or disinfection process is performed on the cell potential detection apparatus 101 or the cell potential detection apparatus 201 before the potentials of the cells are measured. At this time, it is possible to automate the sterilization or disinfection process by using an autoclave (high-pressure washing) process.

In some cases, however, applying the autoclave process to the cell potential detection apparatus 101 or the cell potential detection apparatus 201 may cause the liquid storage unit 112 to peel off from the substrate 111 or may form a gap between the substrate 111 and the liquid storage unit 112 due to the difference in a thermal expansion coefficient between the substrate 111 and the liquid storage unit 112. As a result, there is a possibility of liquid leakage from between the liquid storage unit 112 and the substrate 111.

Further, in the cell potential detection apparatus 301 or the cell potential detection apparatus 401 as well, the liquid storage sealing resin 322 may peel off from the substrate 111 or a gap may be formed therebetween due to a similar cause, in some cases.

Therefore, for example, alcohol washing, pure water washing, a drying process, ultraviolet (UV) sterilization, or the like, may need to be performed, in some cases, instead of the autoclave process, in the cell potential detection apparatuses 101 to 401. This, as a result, increases the number of operations and steps performed by a human, resulting in a decrease in the productivity.

The fifth embodiment makes the autoclave process applicable to a cell potential detection apparatus.

Example of Configuration of Cell Potential Detection Apparatus

Figure 16:
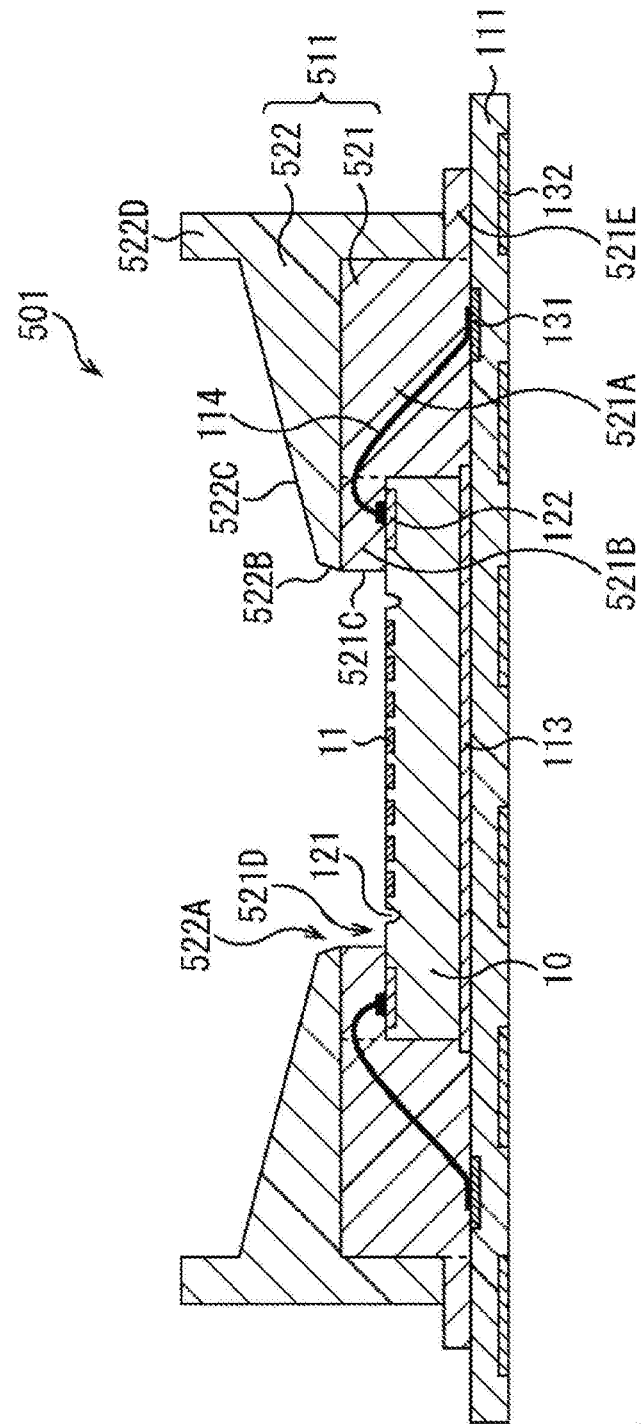
FIG. 16 is a cross-sectional view schematically illustrating a fifth embodiment of the cell potential detection apparatus.
Figure 17:
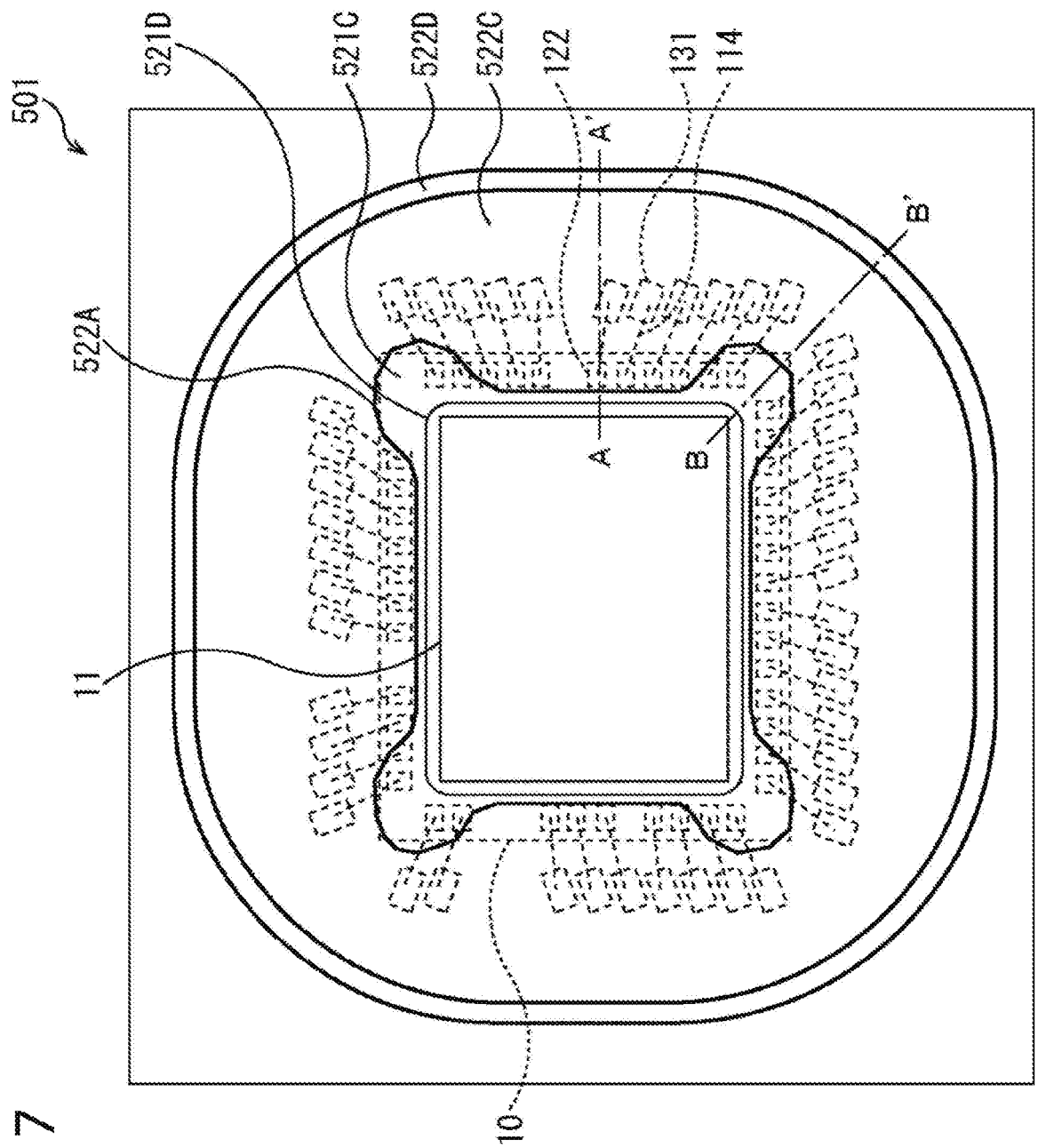
FIG. 17 is a plan view schematically illustrating the fifth embodiment of the cell potential detection apparatus.

FIG. 16 is a cross-sectional view schematically illustrating a cell potential detection apparatus 501 according to the fifth embodiment of the present technology. FIG. 17 is a plan view schematically illustrating the cell potential detection apparatus 501. It is noted that in these figures, parts corresponding to the parts of the cell potential detection apparatus 101 in FIGS. 4 and 5 are denoted with the same reference signs.

The cell potential detection apparatus 501 is different from the cell potential detection apparatus 101 in that a liquid storage sealing section 511 is provided instead of the liquid storage unit 112.

The liquid storage sealing section 511 has a function of storing the culture solution and functions of sealing and protecting the electrical connection section for the cell potential detection chip 10 and the substrate 111, as is the case of the liquid storage unit 112 of the cell potential detection apparatus 101. The liquid storage sealing section 511 includes a sealing and bonding section 521 and a liquid storage member 522. The sealing and bonding section 521 and the liquid storage member 522 are stacked as two layers.

The sealing and bonding section 521 mainly has functions of sealing and protecting the electrical connection section for the cell potential detection chip 10 and the substrate 111 and functions of bonding and fixing the liquid storage member 522.

The sealing and bonding section 521 has a substantially rectangular tube shape and seals the periphery of the electrode section 11 on the detection surface of the cell potential detection chip 10 and the periphery of the cell potential detection chip 10 on the part surface of the substrate 111. Accordingly, the electrical connection section, which includes each pad 122 of the cell potential detection chip 10, each pad 131 of the substrate 111, and each wire 114 connecting the corresponding pads 122 and 131 to each other, is sealed by the sealing and bonding section 521.

Specifically, a rectangular tube section 521A of the sealing and bonding section 521 covers the periphery of the cell potential detection chip 10 on the part surface of the substrate 111. A protrusion section 521B is formed at the upper end of the rectangular tube section 521A and protrudes inward from the inner periphery of the rectangular tube section 521A. The protrusion section 521B covers the periphery of the slit dam 121 on the detection surface of the cell potential detection chip 10. An inclined surface 521C is formed at the inner periphery of the protrusion section 521B. The lower end of the inclined surface 521C protrudes more than the upper end thereof. A substantially rectangular opening section 521D is formed inside the inclined surface 521C. The opening section 521D surrounds the periphery of the slit dam 121 and exposes the electrode section 11 to the outside. A flange 521E, which protrudes outward from the outer periphery of the rectangular tube section 521A, is formed at the lower end of the rectangular tube section 521A. The outer periphery of the flange 521E extends to the outside of each pad 131 of the substrate 111 and the outer periphery of the liquid storage member 522. The upper end of the sealing and bonding section 521 is higher than the upper ends of the wires 114. Each pad 122 of the cell potential detection chip 10, each pad 131 of the substrate 111, and each wire 114 are covered by the sealing and bonding section 521.

With the liquid storage member 522 bonded onto the sealing and bonding section 521, the liquid storage member 522 is fixed to the cell potential detection apparatus 501.

An opening section 522A is formed in the center of the liquid storage member 522. The opening section 522A has a substantially rectangular shape slightly larger than the opening section 521D of the sealing and bonding section 521 and surrounds the opening section 521D. However, as illustrated in FIG. 17, the opening section 522A in the vicinity of four corners extends outward on a substantially circular arc and is more widely spaced from the opening section 521D than other portions.

A substantially vertical surface 522B is formed at the periphery of the opening section 522A. An inclined surface 522C, which is inclined so as to gradually increase in height from the inner periphery toward the outer periphery, is formed at the periphery of the surface 522B. A liquid contact surface with which the culture solution contacts includes the surface 522B and the inclined surface 522C.

The periphery of the inclined surface 522C is surrounded by a wall 522D which extends in the vertical direction. The wall 522D has a rectangular shape with four rounded corners when viewed from above. The upper end of the wall 522D is higher than the outer peripheral portion of the inclined surface 522C. The inner wall of the wall 522D is in contact with the side surface of the rectangular tube section 521A of the sealing and bonding section 521, while the lower end of the wall 522D is in contact with the upper surface of the flange 521E of the sealing and bonding section 521.

In addition, this configuration forms a substantially rectangular dish-shaped liquid storage section with its periphery surrounded by the inclined surface 521C, the surface 522B, the inclined surface 522C, and the inner wall of the wall 522D. The bottom surface of the liquid storage section is an exposure section that includes the electrode section 11 and that is exposed by the opening section 521D on the detection surface of the cell potential detection chip 10. By storing the culture solution in the liquid storage section, the cells arranged on the electrode section 11 can be immersed and cultured in the culture solution.

Figure 18:
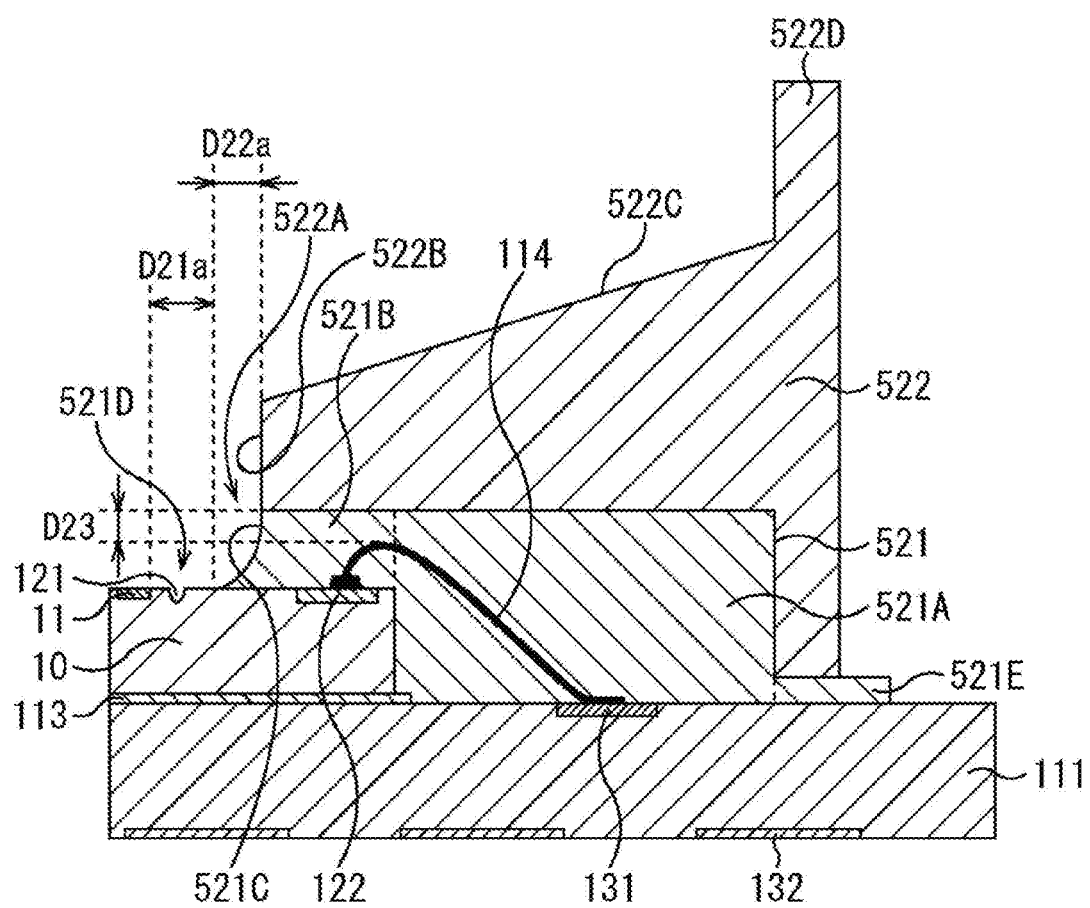
FIG. 18 is an enlarged view schematically illustrating a cross section of an A-A' portion in FIG. 17.
Figure 19:
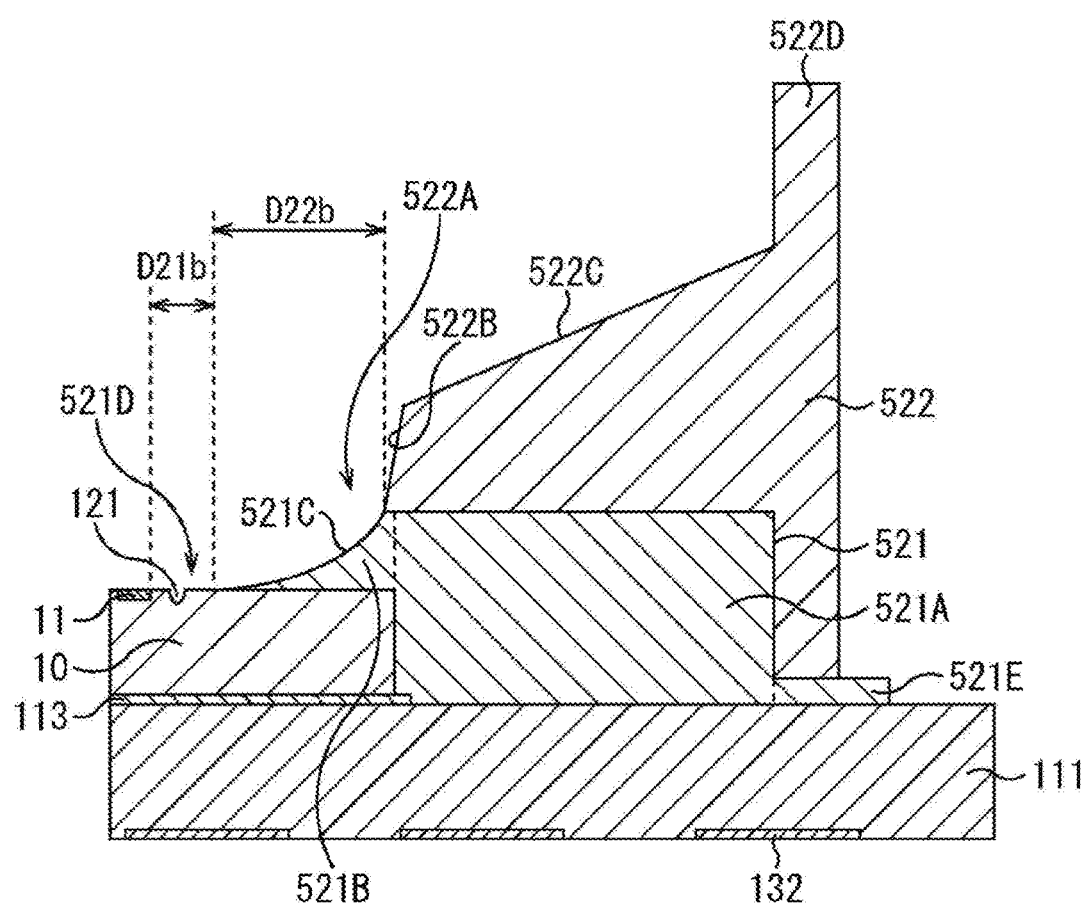
FIG. 19 is an enlarged view schematically illustrating a cross section of a B-B' portion in FIG. 17.

FIG. 18 is an enlarged view schematically illustrating a cross section of an A-A' portion in the vicinity of the center of the side of the electrode section 11 in FIG. 17. FIG. 19 is an enlarged view schematically illustrating a cross section of a B-B' portion in the vicinity of a corner of the electrode section 11 in FIG. 17.

As described above with reference to FIG. 17, the opening section 522A of the liquid storage member 522 in the vicinity of the four corners extends outward on a substantially circular arc and is widely spaced from an opening section A of the sealing and bonding section 521. In accordance with this configuration, the B-B' portion of the inclined surface 521C of the sealing and bonding section 521 has a more gradual and longer inclination than the A-A' portion thereof. That is, since the opening section 522A extends outward on a substantially circular arc in the vicinity of the four corners, the area of the inclined surface 521C, that is, the area of the sealing and bonding section 521 being exposed to the outside is wide in the vicinity of the four corners of the opening section 521D of the sealing and bonding section 521.

This configuration is intended to facilitate the formation of the inner end of the sealing and bonding section 521. Specifically, when the liquid storage member 522 is bonded to the sealing and bonding section 521, air bubbles are likely to be generated in the vicinity of the four corners of the opening section 521D of the sealing and bonding section 521.

By contrast, extending the opening section 522A of the liquid storage member 522 outward on a substantially circular arc in the vicinity of the four corners suppresses generation of air bubbles in the vicinity of the four corners of the opening section 521D of the sealing and bonding section 521 when the liquid storage member 522 is bonded to the sealing and bonding section 521. Further, since the inclined surface 521C is widely exposed to the outside in the vicinity of the four corners of the opening section 521D of the sealing and bonding section 521, it is easy to detect the generation of air bubbles on the inclined surface 521C.

Moreover, air bubbles can easily be removed from the inclined surface 521C by injecting a resin or the like, for example. This configuration improves the airtightness of the sealing and bonding section 521, further strengthening the protection of the electrical connection section for the cell potential detection chip 10 and the substrate 111. Further, in a case where the amount of injected resin varies in production, the four corners of the electrode section 11 are likely to be contaminated with the resin. However, the outward extension on a substantially circular arc allows for a design margin against the resin contamination.

It is noted that in a case where the distance between the outer periphery of the electrode section 11 and the inner periphery of the inclined surface 521C (the outer periphery of the opening section 521D) in the A-A' portion is assumed to be D21a, while the distance between the outer periphery of the electrode section 11 and the inner periphery of the inclined surface 521C in the B-B' portion is assumed to be D21b, the distance D21a and the distance D21b are substantially equal to each other. For example, the distance 21a and the distance D21b are set to equal to or greater than 100 μm so that the resin that is included in the sealing and bonding section 521 does not flow into the electrode section 11.

Further, in a case where the width of the inclined surface 521C (the distance between the inner periphery and the outer periphery of the inclined surface 521C) in the A-A' portion is assumed to be D22a, while the width of the inclined surface 521C in the B-B' portion is assumed to be D22b, the width D22b is equal to or greater than the width D22a. For example, the width D22a is set to a range of 100 to 500 μm, while the width D22b is set to equal to or greater than 500 μm.

Moreover, in a case where the distance between the upper end of the sealing and bonding section 521 and the upper end of the wire 114 is assumed to be D23, the distance D23 is set to equal to or greater than 200 μm, for example.

It is noted that while the upper end of the inclined surface 521C and the lower end of the surface 522B are arranged inside the outer periphery of the cell potential detection chip 10 in the B-B' portion in the example in FIG. 19, the upper end of the inclined surface 521C and the lower end of the surface 522B may be arranged outside the outer periphery of the cell potential detection chip 10.

An example of a combination of the members of the sealing and bonding section 521 and the liquid storage member 522 will be described here.

For example, in a case where a member having a thermal deformation temperature equal to or lower than a temperature (hereinafter referred to as an autoclave temperature) at which the autoclave process is performed is used for the liquid storage member 522, there is a possibility that the liquid storage member 522 is deformed by the autoclave process. Meanwhile, using a member having a post-cure elastic modulus lower than that of the liquid storage member 522 for the sealing and bonding section 521 allows the sealing and bonding section 521 to buffer the deformation of the liquid storage member 522. As a result, even if the liquid storage member 522 is deformed by the autoclave process, this configuration prevents the liquid storage member 522 from peeling off from the sealing and bonding section 521 and a gap between the liquid storage member 522 and the sealing and bonding section 521 from being formed, preventing the culture solution from leaking from the liquid storage section.

For example, the autoclave process is performed under an environment of 121° C., 100% RH (Relative Humidity), and 2 atmospheric pressure. In this case, for example, a member used for the sealing and bonding section 521 has a post-cure elastic modulus of 1 MPa or less, a thermal deformation temperature higher than the autoclave temperature (121° C.), and adhesiveness (an adhesive component), while being harmless and including no component harmful to the cells. For example, a silicone resin or the like having a post-cure elastic modulus of approximately 0.015 MPa is used.

By contrast, a member having a thermal deformation temperature equal to or lower than the autoclave temperature (121° C.) while being harmless and including no component harmful to the cells can be used for the liquid storage member 522. For example, polyethylene (having a thermal deformation temperature of approximately 60° C. to 80° C.), polypropylene (having a thermal deformation temperature of approximately 95° C. to 100° C.), Teflon (registered trademark) (having a thermal deformation temperature of approximately 121° C.), or the like can be used. Needless to say, a Noryl resin or the like having a thermal deformation temperature higher than the autoclave temperature (having a thermal deformation temperature of approximately 191° C.) can also be used for the liquid storage member 522.

Further, for example, using a member having a thermal deformation temperature higher than the autoclave temperature for the liquid storage member 522 can prevent the liquid storage member 522 from being deformed by the autoclave process. For example, using a Noryl resin (having a thermal deformation temperature of approximately 191° C.) for the liquid storage member 522 can suppress the deformation of the liquid storage member 522 by the autoclave process. As a result, this configuration prevents the liquid storage member 522 from peeling off from the sealing and bonding section 521 and a gap between the liquid storage member 522 and the sealing and bonding section 521 from being formed, preventing the culture solution from leaking from the liquid storage section, regardless of the elastic modulus of the sealing and bonding section 521.

It is noted that since most organisms are killed by boiling at 100° C., another possible case is to set the autoclave temperature to 100° C. In this case, a member having a thermal deformation temperature higher than 100° C. while being harmless and including no component harmful to the cells can be used for the liquid storage member 522. For example, in addition to the Noryl resin described above, Teflon (registered trademark) (having a thermal deformation temperature of approximately 121° C.) or the like can be used.

It is noted that in a case where a member having a thermal deformation temperature higher than the autoclave temperature is used for the liquid storage member 522, it is not necessary to consider the post-cure elastic modulus of the sealing and bonding section 521. Therefore, a member having a thermal deformation temperature higher than the autoclave temperature and having adhesiveness while being harmless and including no component harmful to the cells can be used for the sealing and bonding section 521, regardless of the post-cure elastic modulus. For example, in addition to the silicone resin described above, an epoxy resin or the like having a post-cure elastic modulus of approximately 1734 MPa can be used.

Method for Manufacturing Cell Potential Detection Apparatus

Figure 20:
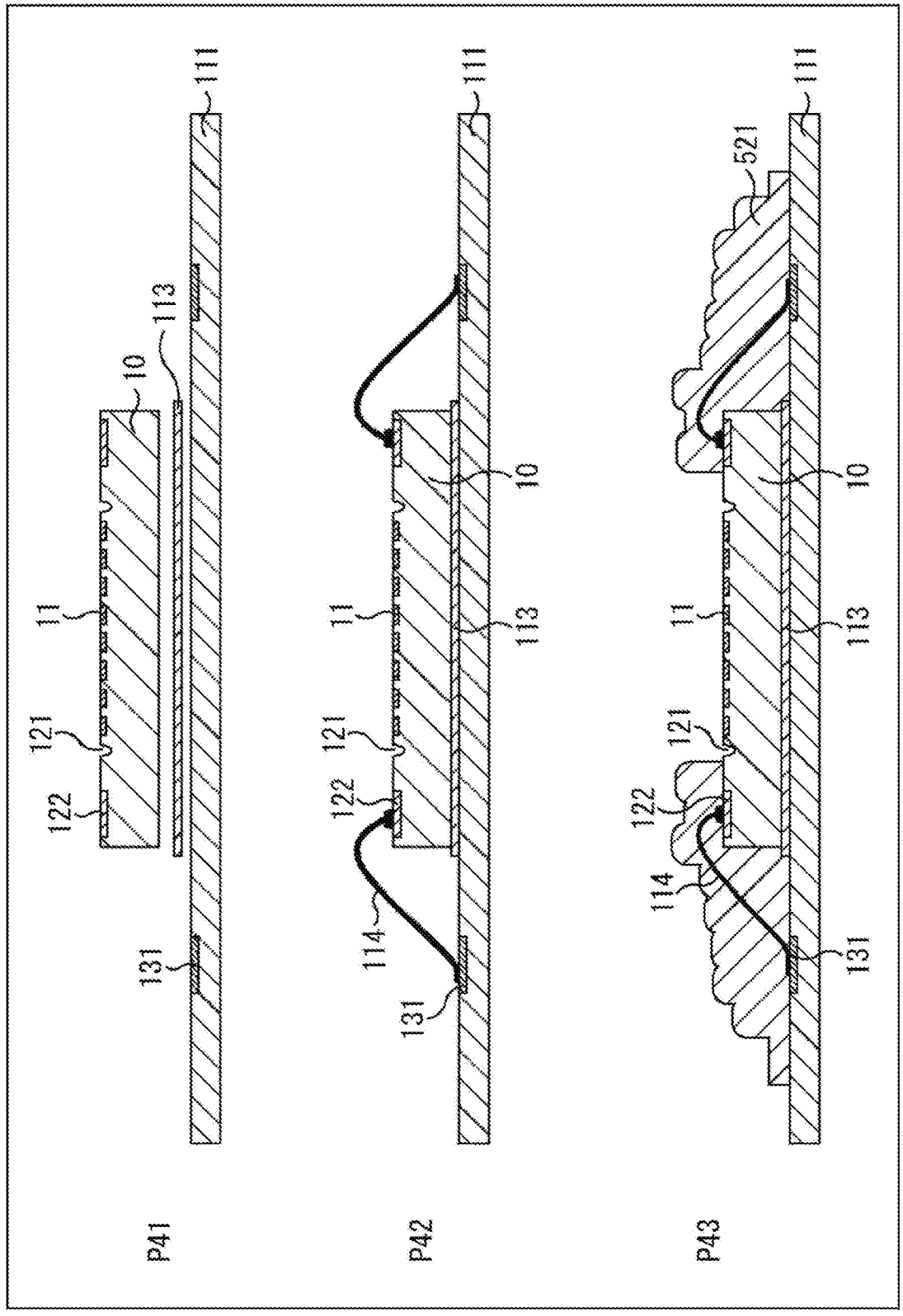
FIG. 20 is a diagram for describing a method for manufacturing the cell potential detection apparatus in FIG. 16.
Figure 21:
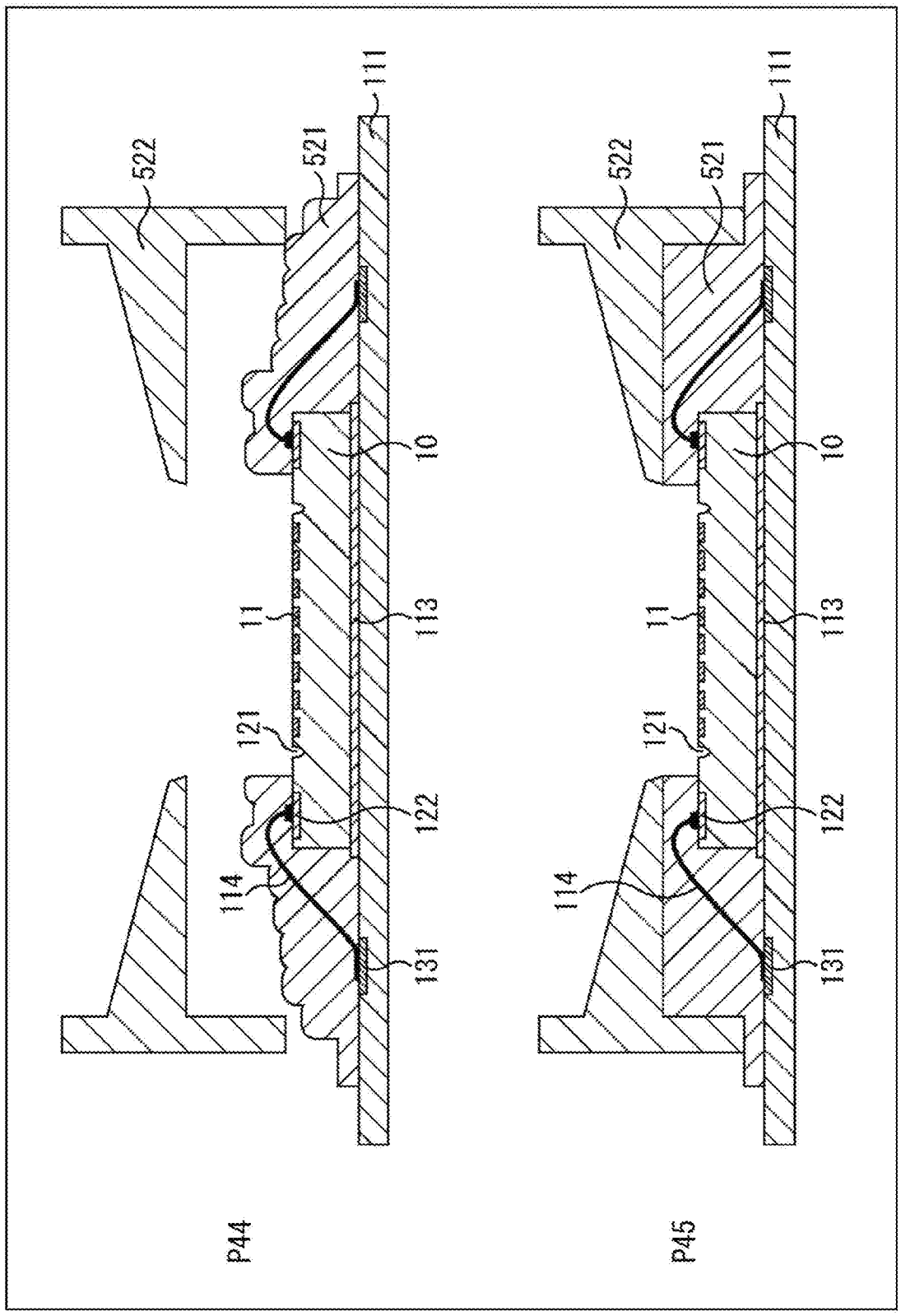
FIG. 21 is a diagram for describing the method for manufacturing the cell potential detection apparatus in FIG. 16.

Next, a method for manufacturing the cell potential detection apparatus 501 will be described with reference to FIGS. 20 and 21. It is noted that in these figures, the description of the reference signs of the parts that are not necessary for the description is omitted as appropriate. Further, the illustration of the external terminals 132 of the substrate 111 is omitted.

Step P41 and step P42 are similar to step P1 and step P2 in FIG. 9 except that the step of forming the resist 251 is omitted. That is, the cell potential detection chip 10 is bonded to the part surface of the substrate 111, and each pad 122 of the cell potential detection chip 10 and each pad 131 of the substrate 111 are connected to each other by a corresponding one of the wires 114.

In step P43, the resin that is included in the sealing and bonding section 521 is dispensed or potted. Accordingly, the electrical connection section for the cell potential detection chip 10 and the substrate 111 is sealed by the sealing and bonding section 521.

In step P44, the liquid storage member 522 is mounted on the sealing and bonding section 521. That is, the liquid storage member 522 is bonded onto the sealing and bonding section 521. At this time, a molded item that has been manufactured in advance by injection molding or the like can be used for the liquid storage member 522.

It is noted that at this time, a part of the resin included in the sealing and bonding section 521 may be provided on the liquid storage member 522 side.

In step P45, the sealing and bonding section 521 and the liquid storage member 522 are cured by thermal curing, ultraviolet curing, or the like. As a result, the sealing and bonding section 521 and the liquid storage member 522 are fixed to the substrate 111.

The cell potential detection apparatus 501 is manufactured as described above.

Here, as for the cell potential detection apparatus 501, the liquid storage sealing section 511 is formed just by dispensing and potting the sealing and bonding section 521, mounting the liquid storage member 522, which is a molded item, on the sealing and bonding section 521, and curing the sealing and bonding section 521 and the liquid storage member 522. Therefore, the productivity is improved as compared with the cell potential detection apparatus 101 and the cell potential detection apparatus 201 in which the liquid storage unit 112 needs to be formed by injection molding, and the cell potential detection apparatus 301 and the cell potential detection apparatus 401 in which, after the ring 321 is bonded, the liquid storage sealing resin 322 needs to be dispensed or potted inside the ring 321.

7. Sixth Embodiment

Next, a seventh embodiment of the present technology will be described with reference to FIG. 22.

Figure 22:
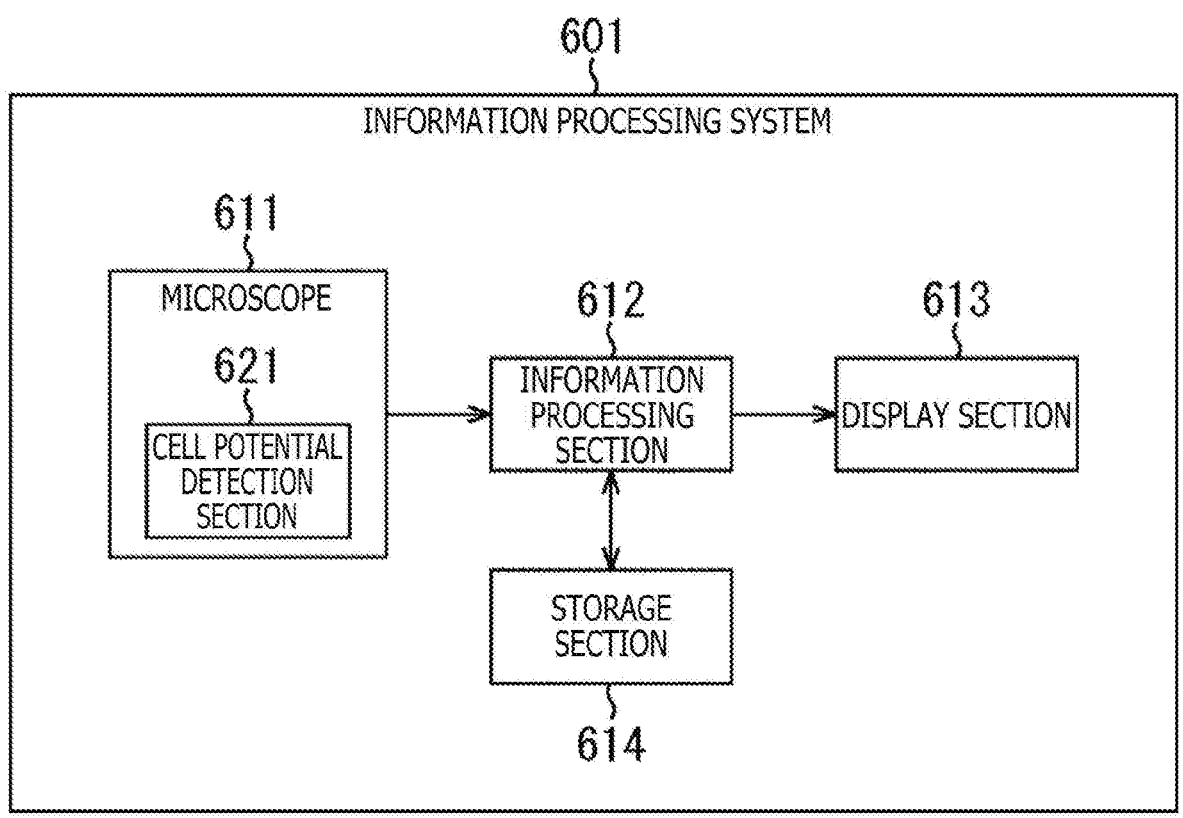
FIG. 22 is a block diagram illustrating an example of a configuration of an information processing system.

FIG. 22 is a block diagram illustrating an example of a configuration of an information processing system 601 according to the seventh embodiment of the present technology.

The information processing system 601 includes a microscope 611, an information processing section 612, a display section 613, and a storage section 614.

The microscope 611 includes a cell potential detection section 621. For example, any of the above-described cell potential detection apparatuses 101 to 501b can be used for the cell potential detection section 621. For example, the microscope 611 photographs a cell to be observed and supplies an observation image obtained to the information processing section 612. Further, the cell potential detection section 621 detects the action potential of the cell to be observed and supplies a detection signal indicating the detection result to the information processing section 612.

The information processing section 612 includes, for example, a computer, a processor, or the like. For example, the information processing section 612 performs various processes on the observation image and the detection signal, generates data indicating the cell observation result, and causes the display section 613 to display the data or causes the storage section 614 to store the data.

The display section 613 includes various displays, for example.

The storage section 614 includes various memories, for example.

It is noted that the processes of the information processing section 612 can be performed by hardware or software. In a case where a series of processes is to be performed by software, a program constituting the software is installed in a computer or the like included in the information processing section 612. Here, examples of the computer include a computer incorporated in dedicated hardware and a general-purpose personal computer, for example, capable of executing various functions with various programs installed therein.

It is noted that the program executed by the computer may be a program that performs processes in chronological order or a program that performs processes in parallel or at necessary timings on occasions of calls or the like.

Further, the program executed by the computer can be provided by recording the program on a removable medium (e.g., the storage section 614) as a package medium or the like, for example. Further, the program can be provided via a wired or wireless transmission medium such as a local area network, the Internet, or digital satellite broadcasting.

8. Modifications

Hereinafter, modifications of the above-described embodiments of the present technology will be described.

For example, a member having a thermal deformation temperature higher than the autoclave temperature may be used for the liquid storage unit 112 of the cell potential detection apparatus 101 or the cell potential detection apparatus 201. This prevents the liquid storage unit 112 from peeling off from the substrate 111 and a gap between the liquid storage unit 112 and the substrate 111 from being formed by the autoclave process, preventing the culture solution from leaking from the liquid storage section.

Further, for example, a member having a thermal deformation temperature higher than the autoclave temperature may be used for the liquid storage sealing resin 322 of the cell potential detection apparatus 301 or the cell potential detection apparatus 401. This prevents the liquid storage sealing resin 322 from peeling off from the substrate 111 and a gap between the liquid storage sealing resin 322 and the substrate 111 from being formed by the autoclave process, preventing the culture solution from leaking from the liquid storage section.

9. Others

In the present specification, a system refers to a collection of a plurality of constituent elements (apparatuses, modules (parts), and the like), and it does not matter whether or not all the constituent elements are within the same housing. Therefore, a plurality of apparatuses stored in separate housings and connected via a network, and one apparatus storing a plurality of modules in one housing are, in either case, the system.

Further, the embodiments of the present technology are not limited to the embodiments described above, and various modifications can be made without departing from the gist of the present technology.

For example, the present technology can be configured as cloud computing in which one function is shared and processed collaboratively among a plurality of apparatuses via a network.

Example of Combination of Configurations

The present technology can also be configured as follows.

(1)
A cell potential detection apparatus including:
a cell potential detection chip including an electrode section configured to detect a potential of a cell;
a member included in a liquid storage section configured to store a culture solution for the cell; and
a film covering a liquid contact surface of the member and being harmless to the cell, the liquid contact surface being configured to contact the culture solution.

(2)
The cell potential detection apparatus according to (1),
in which the member includes an opening section surrounding a periphery of the electrode section and being surrounded by the liquid contact surface, and
the liquid storage section includes
the liquid contact surface, and
an exposure section exposed by the opening section on a surface of the cell potential detection chip on which the electrode section is arranged.

(3)
The cell potential detection apparatus according to (2),
in which the liquid contact surface is surrounded by a wall higher than an outer peripheral portion of the liquid contact surface.

(4)
The cell potential detection apparatus according to (3),
in which the wall is a part of the member.

(5)
The cell potential detection apparatus according to (3),
in which the wall includes a ring surrounding a periphery of the member.

(6)
The cell potential detection apparatus according to any one of (1) to (5),
in which the film includes a film including silicon oxide, silicon oxynitride, aluminum oxide, an epoxy resin, or a silicone resin.

(7)
The cell potential detection apparatus according to any one of (1) to (6),
in which the member includes a resin.

(8)
The cell potential detection apparatus according to any one of (1) to (7), further including:
a substrate on which the cell potential detection chip is mounted,
in which the member seals a connection section configured to electrically connect the cell potential detection chip and the substrate to each other.

(9)
The cell potential detection apparatus according to (8),
in which the connection section includes
a first pad arranged at a periphery of the electrode section on the cell potential detection chip,
a second pad arranged at a periphery of the cell potential detection chip on the substrate, and
a wire connecting the first pad and the second pad to each other.

(10)
A method for manufacturing a cell potential detection apparatus, the method including:
a step of covering, with a film harmless to a cell, a liquid contact surface of a member included in a liquid storage section of the cell potential detection apparatus including a cell potential detection chip including an electrode section configured to detect a potential of the cell, the liquid storage section being configured to store a culture solution for the cell, the liquid contact surface being configured to contact the culture solution.

(11)
An information processing system including:
a cell potential detection section configured to detect a potential of a cell; and
an information processing section configured to process a detection signal of the potential of the cell,
in which the cell potential detection section includes
a cell potential detection chip including an electrode section configured to detect the potential of the cell, the cell potential detection chip being configured to output the detection signal,
a member included in a liquid storage section configured to store a culture solution for the cell, and
a film covering a liquid contact surface of the member and being harmless to the cell, the liquid contact surface being configured to contact the culture solution.

It is noted that the effects described in the present specification are merely examples and are not limitative, and other effects may be provided.

REFERENCE SIGNS LIST

10 Cell potential detection chip, 11 Electrode section, 101 Cell potential detection apparatus, 111 Substrate, 112 Liquid storage unit, 112A Opening section, 112B Inclined surface, 112C Inclined surface, 112D Wall, 114 Wire, 122 Pad, 131 Pad, 201 Cell potential detection chip, 211 Overcoat, 301 Cell potential detection apparatus, 311 Liquid storage sealing section, 321 Ring, 322 Liquid storage sealing resin, 322A Opening section, 322B Inclined surface, 401 Cell potential detection apparatus, 411 Overcoat, 501, 501a, 501b Cell potential detection apparatus, 511 Liquid storage sealing section, 521 Sealing and bonding section, 521C Inclined surface, 521D Opening section, 522 Liquid storage member, 522A Opening section, 522B Surface, 522C Inclined surface, 522D Wall, 601 Information processing system, 611 Microscope, 612 Information processing section, 613 Display section, 621 Cell potential detection section

The invention claimed is:
1. A cell potential detection apparatus, comprising:
a substrate that includes:
a first surface; and
a second surface opposite to the first surface;
a cell potential detection chip that includes:
a first chip surface; and
a second chip surface opposite to the first chip surface, wherein
the second chip surface of the cell potential detection chip is on the first surface of the substrate,
the cell potential detection chip includes an electrode section on the first chip surface, and the electrode section is configured to detect a potential of a cell;
a liquid storage section configured to store a culture solution for the cell, wherein the liquid storage section includes:
a member that includes a liquid contact surface; and
a ring that surrounds a periphery of the member, wherein
the ring is different from the member,
the ring includes an inner wall,
the member is between the electrode section and the inner wall of the ring, and
the ring is in contact with the first surface of the substrate via a seal resin;
a film that covers the liquid contact surface of the member, wherein the liquid contact surface is configured to contact the culture solution; and
a connection section that includes a first pad on the first surface of the substrate, wherein the first pad is between the inner wall of the ring and the cell potential detection chip.

2. The cell potential detection apparatus according to claim 1, wherein
the member further includes an opening section that surrounds periphery of the electrode section,
the liquid contact surface surrounds the opening section,
the liquid storage section further includes exposure section exposed by the opening section, and
the exposure section is on the first chip surface of the cell potential detection chip.

3. The cell potential detection apparatus according to claim 2, wherein
the liquid contact surface is surrounded by the ring, and
the ring is higher than an outer peripheral portion of the liquid contact surface.

4. The cell potential detection apparatus according to claim 1, wherein the film includes at least one of silicon oxide, silicon oxynitride, aluminum oxide, an epoxy resin, or a silicone resin.

5. The cell potential detection apparatus according to claim 1, wherein the member includes a resin.

6. The cell potential detection apparatus according to claim 1, wherein
the member is configured to seal the connection section, and
the connection section is configured to electrically connect the cell potential detection chip and the substrate.

7. The cell potential detection apparatus according to claim 6, wherein the connection section further includes:
a second pad at a periphery of the electrode section on the first chip surface of the cell potential detection chip, and
a wire that connects the first pad and the second pad.

8. The cell potential detection apparatus according to claim 1, further comprising a slit dam on the first chip surface of the cell potential detection chip, wherein the slit dam surrounds a periphery of the electrode section.

9. A method for manufacturing a cell potential detection apparatus, comprising:
covering, with a film, a liquid contact surface of the cell potential detection apparatus, wherein the cell potential detection apparatus includes:
a substrate that includes:
a first surface; and
a second surface opposite to the first surface;
a cell potential detection chip that includes:
a first chip surface; and
a second chip surface opposite to the first chip surface, wherein
the second chip surface of the cell potential detection chip is on the first surface of the substrate,
the cell potential detection chip includes an electrode section on the first chip surface, and
the electrode section is configured to detect a potential of the cell;
a liquid storage section configured to store a culture solution for a cell, wherein the liquid storage section includes:
a member that includes the liquid contact surface; and
a ring that surrounds a periphery of the member, wherein
the ring is different from the member,
the ring includes an inner wall,
the member is between the electrode section and the inner wall,
the ring is in contact with the first surface of the substrate via a seal resin, and
the liquid contact surface is configured to contact the culture solution; and
a connection section that includes a first pad on the first surface of the substrate, wherein the first pad is between the inner wall of the ring and the cell potential detection chip.

10. An information processing system, comprising:
a cell potential detection section configured to detect a potential of a cell,
wherein the cell potential detection section includes:
a substrate that includes:
a first surface; and
a second surface opposite to the first surface;
a cell potential detection chip that includes:
a first chip surface; and
a second chip surface opposite to the first chip surface, wherein
the second chip surface of the cell potential detection chip is on the first surface of the substrate,
the cell potential detection chip includes an electrode section on the first chip surface,
the electrode section is configured to detect the potential of the cell, and
the cell potential detection chip is configured to output a detection signal based on the detected potential of the cell,
a liquid storage section configured to store a culture solution for the cell, wherein the liquid storage section includes:
a member that includes a liquid contact surface; and
a ring that surrounds a periphery of the member, wherein
the ring is different from the member,
the ring includes an inner wall,
the member is between the electrode section and the inner wall, and
the ring is in contact with the first surface of the substrate via a seal resin;
a film that covers the liquid contact surface of the member, wherein the liquid contact surface is configured to contact the culture solution; and
a connection section that includes a first pad on the first surface of the substrate, wherein the first pad is between the inner wall of the ring and the cell potential detection chip; and an information processing section configured to process the detection signal.

* * * * *